United States Patent
Xiao et al.

(10) Patent No.: US 11,501,431 B2
(45) Date of Patent: Nov. 15, 2022

(54) IMAGE PROCESSING METHOD AND APPARATUS AND NEURAL NETWORK MODEL TRAINING METHOD

(71) Applicant: TENCENT TECHNOLOGY (SHENZHEN) COMPANY LIMITED, Guangdong (CN)

(72) Inventors: Fen Xiao, Shenzhen (CN); Jia Chang, Shenzhen (CN); Xuan Zhou, Shenzhen (CN); Ke Zhou Yan, Shenzhen (CN); Cheng Jiang, Shenzhen (CN); Kuan Tian, Shenzhen (CN); Jian Ping Zhu, Shenzhen (CN)

(73) Assignee: TENCENT TECHNOLOGY (SHENZHEN) COMPANY LTD, Shenzhen (CN)

( * ) Notice: Subject to any disclaimer, the term of this patent is extended or adjusted under 35 U.S.C. 154(b) by 365 days.

(21) Appl. No.: 16/905,079

(22) Filed: Jun. 18, 2020

(65) Prior Publication Data
US 2020/0320701 A1    Oct. 8, 2020

Related U.S. Application Data

(63) Continuation of application No. PCT/CN2019/079456, filed on Mar. 25, 2019.

(30) Foreign Application Priority Data

Mar. 27, 2018    (CN) .......................... 201810261926.4

(51) Int. Cl.
*G06T 7/00* (2017.01)
*G06T 7/136* (2017.01)
(Continued)

(52) U.S. Cl.
CPC ............ *G06T 7/0012* (2013.01); *G06T 7/136* (2017.01); *G16H 30/40* (2018.01); *G16H 50/20* (2018.01);
(Continued)

(58) Field of Classification Search
None
See application file for complete search history.

(56) References Cited

U.S. PATENT DOCUMENTS 9,739,783 B1 *    8/2017    Kumar ............. G01N 33/57492
10,181,009 B2 *    1/2019    Yeatman ............... C12Q 1/6886
(Continued)

FOREIGN PATENT DOCUMENTS

CN    105574859 A    5/2016
CN    106780460 A    5/2017
(Continued)

OTHER PUBLICATIONS

Written Opinion of the International Searching Authority dated May 30, 2019 in International Application No. PCT/CN2019/079456.
(Continued)

*Primary Examiner* — Anand P Bhatnagar
(74) *Attorney, Agent, or Firm* — Sughrue Mion, PLLC

(57) ABSTRACT

An image processing method performed by a terminal is provided. A molybdenum target image is obtained, and a plurality of candidate regions are extracted from the molybdenum target image. In the molybdenum target image, a target region is marked in the plurality of candidate regions by using a neural network model obtained by deep learning training, a probability that a lump comprised in the target region is a target lump being greater than a first threshold, a probability that the target lump is a malignant tumor being greater than a second threshold, and the neural network model being used for indicating a mapping relationship
(Continued)

between a candidate region and a probability that a lump comprised in the candidate region is the target lump.

20 Claims, 8 Drawing Sheets

(51) Int. Cl.
    *G16H 50/20*    (2018.01)
    *G16H 30/40*    (2018.01)
    *A61B 6/00*    (2006.01)

(52) U.S. Cl.
    CPC ............... *A61B 6/481* (2013.01); *A61B 6/502* (2013.01); *G06T 2207/20076* (2013.01); *G06T 2207/20081* (2013.01); *G06T 2207/30016* (2013.01); *G06T 2207/30096* (2013.01)

(56) References Cited

U.S. PATENT DOCUMENTS

| | | | | |
|---|---|---|---|---|
| 10,966,693 | B2* | 4/2021 | Tehrani | ..................... A61B 6/12 |
| 2006/0018524 | A1* | 1/2006 | Suzuki | ................... G06V 10/25 |
| | | | | 382/128 |
| 2013/0231258 | A1* | 9/2013 | Wilde | .................. C12Q 1/6886 |
| | | | | 435/6.12 |
| 2017/0016076 | A1* | 1/2017 | Barnett-Itzhaki | .... C12Q 1/6886 |
| 2017/0356055 | A1* | 12/2017 | Barnett-Itzhaki | ...... G16B 20/20 |
| 2019/0300963 | A1* | 10/2019 | Barnett-Itzhaki | ...... G16B 20/00 |
| 2020/0277677 | A1* | 9/2020 | Zhang | .................. C12Q 1/6886 |

FOREIGN PATENT DOCUMENTS

| | | |
|---|---|---|
| CN | 107103187 A | 8/2017 |
| CN | 107616796 A | 1/2018 |
| JP | 2013-525011 A | 6/2013 |

OTHER PUBLICATIONS

Office Action dated Sep. 13, 2021 in Japanese Application No. 2020-543382.

International Search Report for PCT/CN2019/079456 dated May 30, 2019 [PCT/ISA/210].

* cited by examiner

IMAGE PROCESSING METHOD AND APPARATUS AND NEURAL NETWORK MODEL TRAINING METHOD

CROSS-REFERENCE TO RELATED APPLICATION(S)

The disclosure is a bypass continuation application of International Application No. PCT/CN2019/079456, filed on Mar. 25, 2019, which claims priority to Chinese Patent Application No. 201810261926.4, filed with the Chinese Patent Office on Mar. 27, 2018 and entitled "IMAGE PROCESSING METHOD AND APPARATUS AND NEURAL NETWORK MODEL TRAINING METHOD", the disclosures of which are herein incorporated by reference in their entireties.

FIELD

The disclosure relates to the field of computer technologies, and more particularly, to an image processing method, an image processing apparatus, and a neural network model training method.

BACKGROUND

Positioning a suspected malignant tumor by using a molybdenum target image may provide a doctor with a better basis for determining whether a tumor is benign or malignant. However, in the related art, a manual manner is usually used to screen out a suspected malignant tumor from the molybdenum target image. To position a suspected malignant tumor in a manual screening manner, it requires a doctor to have rich experience. In addition, positioning the malignant tumor in the manual screening manner severely affects screening efficiency and positioning accuracy of the suspected malignant tumor.

For the foregoing problems, no effective solutions have been provided so far.

SUMMARY

One or more example embodiments of the disclosure provide an image processing method, an image processing apparatus, and a neural network model training method, that solve the technical problems in the related art that screening efficiency and positioning accuracy of a suspected malignant tumor are relatively low when manual screening is used to position the suspected malignant tumor in a molybdenum target image.

According to an aspect of an example embodiment, provided is an image processing method performed by a terminal. A molybdenum target image is obtained, and a plurality of candidate regions are extracted from the molybdenum target image. In the molybdenum target image, a target region is marked in the plurality of candidate regions by using a neural network model obtained by deep learning training, a probability that a lump comprised in the target region is a target lump being greater than a first threshold, a probability that the target lump is a malignant tumor being greater than a second threshold, and the neural network model being used for indicating a mapping relationship between a candidate region and a probability that a lump comprised in the candidate region is the target lump.

According to an aspect of an example embodiment, provided is a neural network model training method. A sample lump region is obtained, and it is determined a probability that a lump comprised in the sample lump region is a target lump, a probability that the target lump is the malignant tumor being greater than a target threshold. Deep learning training is performed by using a mapping relationship between the sample lump region and the probability that the lump comprised in the sample lump region is the target lump, to obtain the neural network model, wherein, during the deep learning training, a training input parameter comprises the sample lump region, and a training output parameter comprises the probability that the lump comprised in the sample lump region is the target lump.

According to an aspect of an example embodiment, provided is a non-transitory computer-readable storage medium, the storage medium storing a computer program, which, when executed by at least one processor, causes the at least one processor to perform an image processing method, including: obtaining a molybdenum target image; extracting a plurality of candidate regions from the molybdenum target image; and marking, in the molybdenum target image, a target region in the plurality of candidate regions by using a neural network model obtained by deep learning training, a probability that a lump included in the target region is a target lump being greater than a first threshold, a probability that the target lump is a malignant tumor being greater than a second threshold, and the neural network model being used for indicating a mapping relationship between a candidate region and a probability that a lump included in the candidate region is the target lump.

According to an aspect of an example embodiment, provided is an image processing apparatus, the apparatus being installed in a terminal and configured to perform the above image processing method.

According to an aspect of an example embodiment, provided is an electronic apparatus, including at least one memory and at least one processor, the at least one memory storing a computer program, and the at least one processor being configured to execute the computer program to perform the above neural network model training method.

According to an aspect of an example embodiment, provided is an image processing apparatus, including: at least one memory configured to store program code; and at least one processor configured to read the program code and operate as instructed by the program code, the program code including: obtaining code configured to cause at least one of the at least one processor to obtain a molybdenum target image; extracting code configured to cause at least one of the at least one processor to extract a plurality of candidate regions from the molybdenum target image; and marking code configured to cause at least one of the at least one processor to mark, in the molybdenum target image, a target region in the plurality of candidate regions by using a neural network model obtained by deep learning training, a probability that a lump included in the target region is a target lump being greater than a first threshold, a probability that the target lump is a malignant tumor being greater than a second threshold, and the neural network model being used for indicating a mapping relationship between a candidate region and a probability that a lump included in the candidate region is the target lump.

In the example embodiments of the disclosure, a terminal obtains a molybdenum target image, the terminal extracts a plurality of candidate regions from the molybdenum target image, and the terminal marks, in the molybdenum target image, a target region in the plurality of candidate regions by using a neural network model obtained by deep learning training. A probability that a lump included in the target region is a target lump is greater than a first threshold, a probability that the target lump is a malignant tumor is greater than a second threshold, and the neural network model is used for indicating a mapping relationship between the candidate region and a probability that a lump included in the candidate region is the target lump. A target lump region is automatically marked in the molybdenum target image without manual participation, thereby solving the technical problem in the related art that screening efficiency and positioning accuracy of a suspected malignant tumor are relatively low because the suspected malignant tumor in the molybdenum target image is positioned by manual screening, and achieving a technical effect of improving the screening efficiency and the positioning accuracy of the suspected malignant tumor.

BRIEF DESCRIPTION OF THE DRAWINGS

The accompanying drawings described herein are used for providing further understanding for the disclosure and constitute a part of the disclosure. Example embodiments of the disclosure and descriptions thereof are used for explaining the disclosure and do not constitute an improper limitation to the disclosure.

DETAILED DESCRIPTION

To make a person skilled in the art better understand solutions of the disclosure, the following clearly and completely describes the technical solutions in example embodiments of the disclosure with reference to the accompanying drawings. Apparently, the described example embodiments are merely some rather than all of the embodiments of the disclosure. All other embodiments that may be obtained by a person skilled in the art based on the example embodiments of the disclosure without creative efforts shall fall within the protection scope of the disclosure.

In the specification, claims, and accompanying drawings of the disclosure, the terms "first", "second", and so on are intended to distinguish between similar objects rather than indicating a specific order. The data termed in such a way are interchangeable in proper circumstances, so that the example embodiments of the disclosure described herein may be implemented in other orders than the order illustrated or described herein. Moreover, the terms "include", "contain" and any other variants mean to cover non-exclusive inclusion. For example, a process, method, system, product, or device that includes a list of operations or units is not necessarily limited to those expressly listed operations or units, but may include other operations or units not expressly listed or inherent to such a process, method, system, product, or device.

First, some nouns or terms that appear during descriptions of the example embodiments of the disclosure are applicable to the following explanations:

A molybdenum target image is an image obtained by capturing an image of tissue of a human body part. The tissue of a human body part may be captured by using a soft X-ray, and after being captured, a procedure such as sensitization, development, and fixation may be performed by using a film. For example, a molybdenum target image obtained by capturing breast tissue is a breast molybdenum target image.

According to an aspect of example embodiments of the disclosure, an image processing method is provided.

Figure 1:
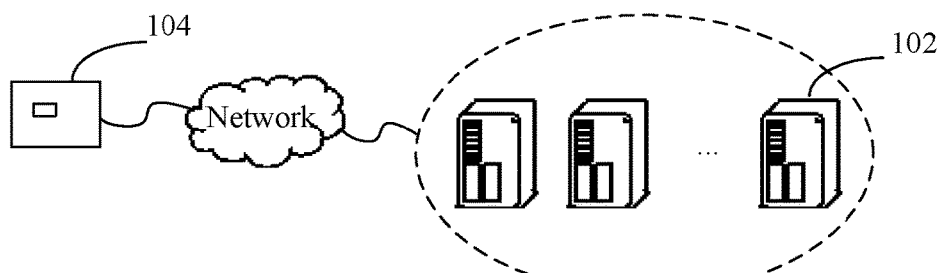
FIG. 1 is a schematic diagram of a hardware environment of an image processing method according to an example embodiment of the disclosure.

Optionally, in an example embodiment, the image processing method may be applied to a hardware environment including a server 102 and a terminal 104 shown in FIG. 1. As shown in FIG. 1, the server 102 is connected to the terminal 104 through a network. The network includes, but is not limited to, a wide area network, a metropolitan area network, or a local area network. The terminal 104 may be a molybdenum target photography apparatus, and the type of the molybdenum target photography apparatus is not specifically limited in the disclosure.

Optionally, the image processing method in an example embodiment of the disclosure may be performed by the terminal 104. Optionally, the image processing method performed by the terminal 104 in an example embodiment of the disclosure may alternatively be performed by a client installed on the terminal 104. A specific process of the image processing method performed by the terminal 104 in an example embodiment of the disclosure may be: obtaining, by the terminal 104, a molybdenum target image; extracting, by the terminal 104, a plurality of candidate regions from the molybdenum target image; and marking, by the terminal 104 in the molybdenum target image, a target region in the plurality of candidate regions by using a neural network model obtained by deep learning training. The marking of the target region is based on a probability that a lump included in the target region is a target lump being greater than a first threshold, and a probability that the target lump is a malignant tumor being greater than a second threshold. The neural network model is used for indicating a mapping relationship between the candidate region and a probability that a lump included in the candidate region is the target lump. Optionally, the terminal 104 may further output the molybdenum target image in which the target region is marked.

Optionally, the image processing method in an example embodiment of the disclosure may be jointly performed by the server 102 and the terminal 104. A specific process of the image processing method jointly performed by the server 102 and the terminal 104 in an example embodiment of the disclosure may be: obtaining, by the terminal 104, a molybdenum target image; transmitting, by the terminal 104, the molybdenum target image to the server 102; extracting, by the server 102, a plurality of candidate regions from the molybdenum target image; marking, by the server 102 in the molybdenum target image, a target region in the plurality of candidate regions by using a neural network model obtained by deep learning training, a probability that a lump included in the target region is a target lump being greater than a first threshold, a probability that the target lump is a malignant tumor being greater than a second threshold, and the neural network model being used for indicating a mapping relationship between the candidate region and a probability that a lump included in the candidate region is the target lump; transmitting, by the server 102, the molybdenum target image in which the target region is marked to the terminal 104; and outputting, by the terminal 104, the molybdenum target image in which the target region is marked.

Figure 2:
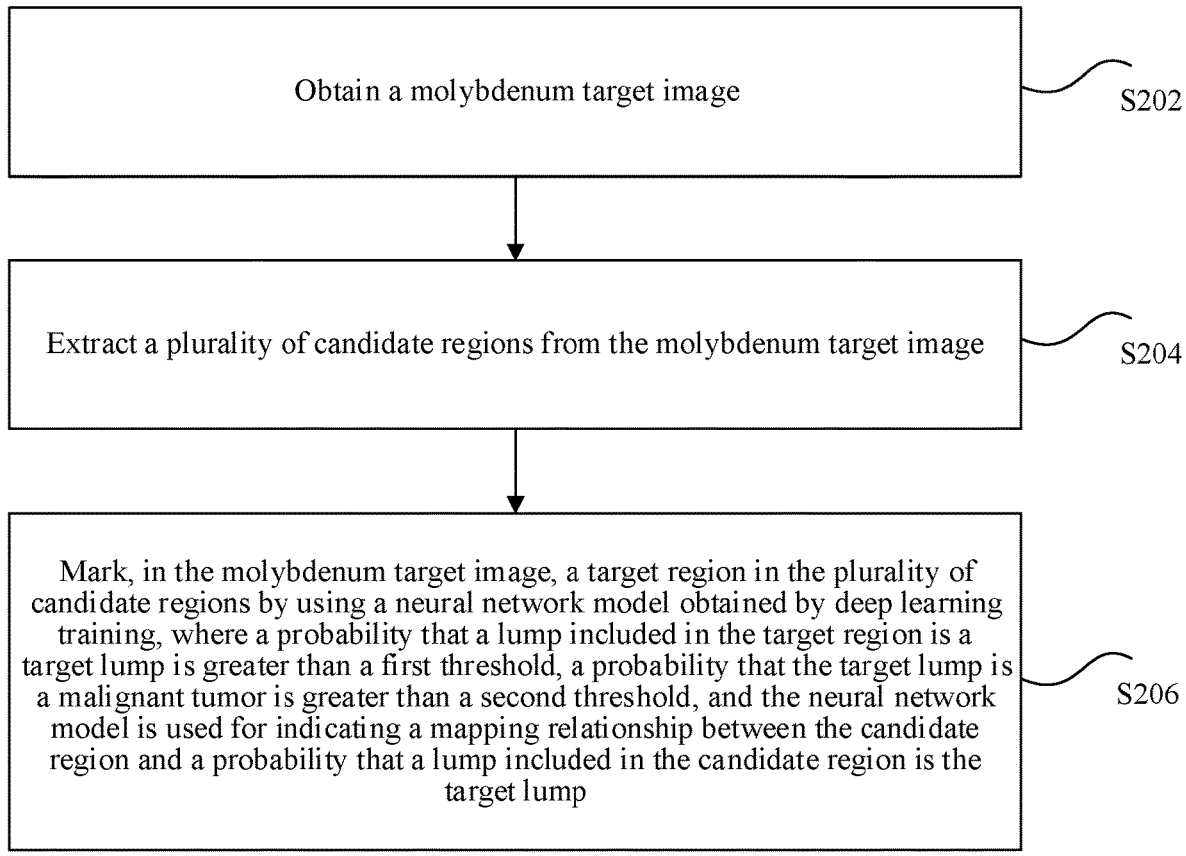
FIG. 2 is a flowchart of an optional image processing method according to an example embodiment of the disclosure.

In the example embodiments of the disclosure, the image processing method being performed by the terminal is used as an example to describe the image processing method with reference to FIG. 2. However, this is merely an example and the disclosure is not limited thereto.

FIG. 2 is a flowchart of an optional image processing method according to an example embodiment of the disclosure. As shown in FIG. 2, the method may include the following operations:

Operation S202. A terminal obtains a molybdenum target image.

Operation S204. The terminal extracts a plurality of candidate regions from the molybdenum target image.

Operation S206. The terminal marks, in the molybdenum target image, a target region in the plurality of candidate regions by using a neural network model obtained by deep learning training, where a probability that a lump included in the target region is a target lump is greater than a first threshold, a probability that the target lump is a malignant tumor is greater than a second threshold, and the neural network model is used for indicating a mapping relationship between the candidate region and a probability that a lump included in the candidate region is the target lump.

Through operation S202 to operation S206, the terminal obtains a molybdenum target image, the terminal extracts a plurality of candidate regions from the molybdenum target image, and the terminal marks, in the molybdenum target image, a target region in the plurality of candidate regions by using a neural network model obtained by deep learning training. The marking is based on a probability that a lump included in the target region is a target lump being greater than a first threshold, and a probability that the target lump is a malignant tumor being greater than a second threshold. The neural network model is used for indicating a mapping relationship between the candidate region and a probability that a lump included in the candidate region is the target lump. A suspected malignant tumor region is automatically marked in the molybdenum target image without manual participation, thereby solving the technical problem in the related art that screening efficiency and positioning accuracy of a suspected malignant tumor are relatively low because the suspected malignant tumor in the molybdenum target image is positioned by manual screening, and achieving a technical effect of improving the screening efficiency and the positioning accuracy of the suspected malignant tumor.

In the technical solution provided in operation S202, the molybdenum target image may be an image obtained by capturing (e.g., photographing) tissue of a human body part. The type of the molybdenum target image is not specifically limited in the disclosure. For example, the molybdenum target image may be a breast molybdenum target image, e.g., an image obtained by photographing breast tissue.

The terminal obtains the molybdenum target image. In an optional example, the terminal may include a molybdenum target photography apparatus, and the type or model of the molybdenum target photography apparatus is not specifically limited in the disclosure. According to the example embodiment of the disclosure, the terminal directly obtains the molybdenum target image obtained by using the molybdenum target photography apparatus.

In another optional example, the terminal may be a device such as a smartphone and a tablet, and the terminal may be in a communication connection with the molybdenum target photography apparatus. The communication connection may be a wired connection, or may be a wireless connection. According to the example embodiment of the disclosure, the molybdenum target photography apparatus may be used to take a picture to obtain the molybdenum target image, and then transmit the molybdenum target image to the terminal by using the communication connection, so that the terminal obtains the molybdenum target image.

In the disclosure, the terminal may obtain the molybdenum target image in any other manners, which are not individually illustrated herein.

In the technical solution provided in operation S204, there may be no lump region or may be a lump region in the molybdenum target image obtained by the terminal. The molybdenum target image may include, if any, one or more lump regions. A lump included in the lump region in the molybdenum target image may be a suspected malignant tumor, or may be a non-suspected malignant tumor. According to the disclosure, the lump region including the suspected malignant tumor in the molybdenum target image may be marked, to achieve the objective of inspecting and positioning the suspected malignant tumor.

Optionally, after obtaining the molybdenum target image, the terminal may preprocess the molybdenum target image to reduce noise and position a target image. The target image may be an image including a human body part in the molybdenum target image. For example, a target image in a breast molybdenum target image is an image including a breast. A process of preprocessing the molybdenum target image may specifically include: removing, by the terminal, noise in the molybdenum target image, to obtain a denoised molybdenum target image; and extracting, by the terminal, a target image from the denoised molybdenum target image. The target image is an image including a human body part.

A technical means used for removing the noise in the molybdenum target image and a technical means used for extracting the target image from the denoised molybdenum target image are not specifically limited in the disclosure. For example, in an optional example, a gray range of pixel values in the molybdenum target image may be stretched to 0 to 255 by using a normalization method through linear stretching, so as to improve robustness of subsequent processing of the molybdenum target image. The target image may be extracted from the molybdenum target image by using a morphological opening operation and binarization. For example, a breast region is extracted from a breast molybdenum target image, and background such as a label in the molybdenum target image may be further removed. The morphological opening operation may remove fine tissue and noise in the molybdenum target image. In a segmentation process of the molybdenum target image, binary classification may be performed by using an Otsu's method, thereby effectively extracting an image region including a human body part, for example, a breast tissue region. The molybdenum target image may be further converted into a histogram, and histogram equalization is performed, thereby improving robustness of subsequent processing of the molybdenum target image histogram. A bilateral filter may be further used to remove noise that may exist in human body part tissue (for example, breast tissue), and regional homogeneity is improved to some extent. The bilateral filter does not destroy a segmentation edge.

The molybdenum target image is preprocessed by the terminal, and the noise in the molybdenum target image may be removed, so that accuracy of analytical processing on the molybdenum target image is improved, thereby achieving an effect of improving screening accuracy of a suspected malignant tumor. In addition to the foregoing technical means, other denoising processing may also be performed on the molybdenum target image in the disclosure, so as to remove the noise in the molybdenum target image and extract the target image from the denoised molybdenum target image. Such denoising processing is not illustrated herein.

After obtaining the molybdenum target image, the terminal may extract the plurality of candidate regions from the molybdenum target image by using an image segmentation technology, so that the target region including a suspected malignant tumor is determined from the plurality of candidate regions.

Optionally, after preprocessing the molybdenum target image to obtain the target image, the terminal may segment the target image, so as to extract the plurality of candidate regions from the target image.

Optionally, the extracting, by the terminal, a plurality of candidate regions from the molybdenum target image may include the following process: determining an image segmentation threshold; and segmenting the molybdenum target image according to the image segmentation threshold(s), to obtain the plurality of candidate regions.

In an optional example, dimensions of the molybdenum target image may be reduced by using a two-dimensional (2D)-wavelet transform (for example, a series is 3). For a low-detail image, statistics on the histogram of the molybdenum target image are collected after normalization, and image segmentation is performed based on the histogram. Optionally, the histogram may be segmented by using a genetic algorithm. The image segmentation threshold may be determined by using the genetic algorithm, and a specific determining process may be described as follows: a binary code form is used for a gene, and a length is equal to the quantity of gray scales (0 to 255), that is, a binary code length is 256. When a value of a bit in the binary code is 0, the gray scale corresponding to the bit is the image segmentation threshold. A value function of the genetic algorithm takes a maximum inter-class variance and a minimum intra-class variance as a standard. A general genetic algorithm procedure is used, and three processes of iterative selection, crossover, and aberrance are repeated after population initialization, until convergence is achieved (for example, the quantity of initial populations is 30, the quantity of iterations iteration is 40, a selectivity is 10%, a crossing-over rate is 80%, and an aberration rate is 10%). An optimum binary code may be determined by using the genetic algorithm, and the image segmentation threshold may be determined according to the binary code. For example, values of the fifth bit and the seventh bit of the binary code are 0, and the image segmentation thresholds are 32 and 128 respectively. Gray levels of pixel values of the molybdenum target image may be classified into three gray scales according to the image segmentation thresholds: a gray value lower than 32, a gray value between 32 and 128, and a gray value higher than 128. The molybdenum target image is segmented according to the determined image segmentation threshold, and the plurality of candidate regions may be obtained.

Optionally, the segmenting, by the terminal, the molybdenum target image according to the image segmentation threshold(s), to obtain the plurality of candidate regions may include: ranking, by the terminal according to gray scales, a plurality of image regions obtained by segmenting the molybdenum target image according to the image segmentation threshold, where the gray scales are related to the image segmentation threshold; and determining, by the terminal, image regions whose ranks are equal to or higher than a fourth threshold in the plurality of image regions as the candidate regions. The fourth threshold may be set or adjusted according to actual requirements, and is not specifically limited herein.

Optionally, in a case that a quantity of image regions whose ranks are equal to or are higher than the fourth threshold in the plurality of image regions is greater than a fifth threshold, the segmenting, by the terminal, the molybdenum target image according to the image segmentation threshold, to obtain the plurality of candidate regions may include: ranking, by the terminal according to areas of the image regions, the image regions whose ranks are equal to or are higher than the fourth threshold in the plurality of image regions; and determining, by the terminal, image regions whose areas are greater than a sixth threshold in the image regions whose ranks are equal to or are higher than the fourth threshold in the plurality of image regions as the candidate regions, where a quantity of the determined image regions whose areas are greater than the sixth threshold is equal to the fifth threshold, among the image regions whose ranks are equal to or higher than the fourth threshold in the plurality of image regions. The fifth threshold and the sixth threshold may be set or adjusted according to actual requirements, and are not specifically limited herein.

For example, the image segmentation thresholds determined by using the genetic algorithm are 32 and 128 respectively, gray levels of pixel values of the molybdenum target image may be classified into three gray scale ranges in descending order according to the image segmentation thresholds, that is, a gray scale range in which a gray value higher than 128, a gray scale range in which a gray value is between 32 and 128, and a gray scale range in which a gray value is lower than 32. The molybdenum target image is segmented according to the determined image segmentation thresholds, and there may be 5 image regions whose gray values are higher than 128, 10 image regions whose gray values are between 32 and 128, and 50 image regions whose gray values are lower than 32. The plurality of image regions obtained by segmenting the molybdenum target image according to the image segmentation thresholds are ranked according to a descending order of the gray scales as follows: 5 image regions whose gray values are higher than 128, 10 image regions whose gray values are between 32 and 128, and 50 image regions whose gray values are lower than 32. It is assumed that the fourth threshold is 2. In this case, the 5 image regions whose gray values are higher than 128 and the 10 image regions whose gray values are between 32 and 128 (a total of 15 image regions) may be determined as the candidate regions (that is, according to ranks 1 and 2).

In an example application scenario, to improve accuracy of positioning and screening of a suspected malignant tumor, the quantity of candidate regions may need to be preset. In an optional example, it is assumed that there are 10 predetermined candidate regions, that is, the fifth threshold is 10. In this case, the quantity of image regions whose ranks are equal to or higher than the fourth threshold of 2 (the 5 image regions whose gray values are higher than 128 and the 10 image regions whose gray values are between 32 and 128, 15 image regions in total) is greater than 10, and 10 image regions need to be obtained from the 15 image regions. The 15 image regions need to be ranked according to a descending order of areas of the image regions, and then the image regions whose areas are in the top 10 are taken as the candidate regions.

After the molybdenum target image is segmented by using the image segmentation technology, the plurality of candidate regions may be accurately obtained, thereby achieving an effect of improving the accuracy of positioning and screening of the suspected malignant tumor.

Optionally, the segmenting the molybdenum target image according to the image segmentation threshold to obtain the plurality of candidate regions may further include: disconnecting, by the terminal, a connection line that is used for indicating a tissue connection of a human body part in each image region in the plurality of image regions obtained by segmenting the molybdenum target image according to the image segmentation threshold, to obtain the plurality of candidate regions.

A technical means used for disconnecting the connection line that is used for indicating the tissue connection of the human body part in each image region may include but is not limited to a morphological opening operation. The molybdenum target image is the image obtained by photographing tissue of a human body part, the molybdenum target image may include connection lines used for indicating tissue connections of the human body part, and the connection lines affect accuracy of image segmentation performed on the molybdenum target image. Therefore, the terminal may disconnect the connection line that is used for indicating the tissue connection of the human body part in each image region in the plurality of image regions obtained by segmenting the molybdenum target image according to the image segmentation threshold, to improve accuracy of the plurality of obtained candidate regions, thereby achieving an effect of improving the accuracy of positioning and screening of the suspected malignant tumor.

In the technical solution provided by operation S206, after extracting the plurality of candidate regions from the molybdenum target image, the terminal may determine the target region from the plurality of candidate regions and mark the target region in the molybdenum target image. The probability that the lump included in the target region is the target lump is greater than the first threshold, and the probability that the target lump is a malignant tumor is greater than the second threshold, that is, the target lump in the target region in the example embodiment of the disclosure is determined as a suspected malignant tumor. The first threshold and the second threshold may be set or adjusted according to actual requirements, and are not specifically limited herein. A mark form for marking the target region in the molybdenum target image is not specifically limited in the disclosure. For example, a frame line may be added to the target region.

Optionally, the marking, by the terminal in the molybdenum target image, a target region in the plurality of candidate regions by using a neural network model obtained by deep learning training may include: obtaining, by using the neural network model, a probability that a lump included in each candidate region in the plurality of candidate regions is the target lump, where the neural network model is used for indicating a mapping relationship between the candidate region and the probability that the lump included in the candidate region is the target lump; and determining a candidate region whose probability is greater than the first threshold as the target region, and marking the target region in the molybdenum target image.

The neural network model obtained by deep learning training may be used for indicating the mapping relationship between the candidate region and the probability that the lump included in the candidate region is the target lump. To be specific, by inputting the candidate region into the neural network model, the terminal may obtain the probability that the lump included in the candidate region is the target lump. According to the example embodiment of the disclosure, through the neural network model obtained by deep learning training, the probability that the lump included in the candidate region is the target lump is obtained, and the target region including the target lump is rapidly and accurately screened out and positioned from the molybdenum target image without manual participation, thereby greatly improving efficiency of screening and positioning of the suspected malignant tumor.

Optionally, before obtaining the molybdenum target image, the terminal may first perform deep learning training to obtain a trained neural network model, thereby rapidly and accurately obtaining the probability that the lump included in each candidate region is the target lump by using the trained neural network model, so that the target region including the target lump is further accurately screened out and positioned from the molybdenum target image. A specific training process may include: performing, by the terminal, deep learning training by using a mapping relationship between a sample lump region and a probability that a lump included in the sample lump region is the target lump, to obtain the trained neural network model, where during the deep learning training, a training input parameter may include the sample lump region, and a training output parameter may include the probability that the lump included in the sample lump region is the target lump.

After the terminal performs deep learning training by using the mapping relationship between the sample lump region and the probability that the lump included in the sample lump region is the target lump, the trained neural network model may be obtained. During the deep learning training, a larger quantity of sample lump regions indicates higher accuracy of the neural network model, so that accuracy of the target region determined by using the trained neural network model is higher.

Optionally, the sample lump region may include a first lump region and a second lump region. A lump included in the first lump region is the target lump, and a lump included in the second lump region is a non-target lump or the second lump region does not include a lump (that is, the second lump region does not include the target lump). The performing, by the terminal, deep learning training by using a mapping relationship between a sample lump region and a probability that a lump included in the sample lump region is the target lump, to obtain the neural network model may include: performing, by the terminal, deep learning training by using a mapping relationship between the first lump region and a probability that the lump included in the first lump region is the target lump and a mapping relationship between the second lump region and a probability that the lump included in the second lump region is the target lump, to obtain the trained neural network model.

In an optional example, domestic hospital data may be used, and experts may label the data (e.g., more than 2200 pieces). Suspected malignant tumors are used as positive samples, and remaining obvious benign tumors and background regions are used as negative samples. Because the data is molybdenum target images, data enhancement of flipping and cropping is mainly performed, while data enhancement of color space is not required; in addition, the inputted malignant tumor sample needs to include an entire lump region and be surrounded by a small background region. After data enhancement, the samples are inputted as training data of the disclosure into an inception V3 model for training, and the quantity of output categories of the model is reset to 2. During weight initialization of the model, an ImageNet dataset is used first, then a public dataset DDSM is used, and finally the training data of the disclosure is used for transfer learning to obtain a final model weight. For example, a descent algorithm uses RMSprop, a size of batch processing is 64, an initial learning rate is 0.01, and a maximum quantity of iterations is 100000. After the model training is completed, for any inputted candidate region, a probability of the candidate region being a suspected malignant tumor may be obtained through calculation based on the trained neural network model. Generally, a candidate region is considered as a suspected malignant tumor when the probability is greater than 0.5.

When the terminal performs deep learning training by using sample lump regions, the sample lump regions may include the following types: a first lump region including the target lump, a second lump region including a non-target lump, and an image region without any lump, and the quantity of samples in each type is equivalent, so that accuracy of the neural network model obtained by deep learning training is improved.

The neural network model obtained by the deep learning training process may accurately determine the probability that the lump included in each candidate region is the target lump. It is assumed that the first threshold is 0.5. In this case, if it is determined, by using the neural network model obtained by deep learning training, that a probability of a lump included in a candidate region being the target lump is greater than 0.5, the candidate region may be determined as the target region, and the target region is marked in the molybdenum target image. There may be one or more target regions determined by using the method, or there is no target region in the molybdenum target image. According to the example embodiment of the disclosure, by using the neural network model obtained by deep learning training, the target region including the target lump is determined from the plurality of candidate regions, and the suspected malignant tumor may be rapidly and accurately screened out and positioned without manual participation, thereby solving the technical problem in the related art that screening efficiency and positioning accuracy of the suspected malignant tumor are relatively low because the suspected malignant tumor in the molybdenum target image is positioned by manual screening, thereby implementing a technical effect of improving the screening efficiency and the positioning accuracy of the suspected malignant tumor.

Optionally, for the determined target regions including the target lump, the terminal may remove an overlapping region by using a non-maximum suppression method, that is, in a case that there is a plurality of candidate regions whose probabilities of including a target lump (or a suspected malignant tumor) are greater than the first threshold, the determining a candidate region whose probability of including a target lump is greater than the first threshold as the target region includes: ranking, by the terminal according to values of the probabilities, the plurality of candidate regions whose probabilities of including a target lump are greater than the first threshold; calculating, by the terminal, an overlapping area between a first candidate region and each second candidate region respectively, where the first candidate region is a candidate region with the largest probability in the plurality of candidate regions whose probabilities of including the target lump are greater than the first threshold, and the second candidate region is a candidate region other than the first candidate region in the plurality of candidate regions whose probabilities of including the target lump are greater than the first threshold; deleting, by the terminal, any second candidate region whose overlapping area with the first candidate region is greater than a third threshold from the plurality of candidate regions whose probabilities of including the target lump are greater than the first threshold, to obtain one or more remaining candidate regions; and determining, by the terminal, the one or more remaining candidate regions as the target region. The third threshold may be set or adjusted according to actual requirements, and is not specifically limited herein.

For example, it is assumed that 10 candidate regions are extracted from the molybdenum target image, and the neural network model obtained by deep learning training obtains probabilities that lumps included in the 10 candidate regions are the target lump, and the probabilities are: 0.9, 0.2, 0.4, 0.6, 0.7, 0.3, 0.0, 0.2, 0.8, and 0.1. When the first threshold is 0.5, candidate regions whose probabilities of including the target lump are greater than 0.5 in the 10 candidate regions are the candidate regions corresponding to the probabilities of 0.9, 0.6, 0.7, and 0.8. In the four candidate regions, an overlapping area between the candidate region whose probability is 0.6 and the candidate region whose probability is 0.9 is 2, an overlapping area between the candidate region whose probability is 0.7 and the candidate region whose probability is 0.9 is 5, and an overlapping area between the candidate region whose probability is 0.8 and the candidate region whose probability is 0.9 is 10. It is assumed that the third threshold is 6. In this case, the candidate region whose probability is 0.8 is deleted from the four candidate regions, and the remaining candidate regions may be determined as the target regions.

According to the example embodiment of the disclosure, the overlapping region in the target region is removed by using the non-maximum suppression method, so that a false alarm rate may be reduced, thereby achieving an effect of improving accuracy of positioning the suspected malignant tumor.

Optionally, after determining the target region from the plurality of candidate regions, and marking the target region in the molybdenum target image, the terminal may output the molybdenum target image marked with the target region, so that a doctor may clearly and intuitively determine a specific position of the target lump and a size of the target lump.

The image processing method according to the example embodiment of the disclosure may be applied to the field of medical diagnosis, for example, early screening of a breast cancer. When breast cancer is screened by using the image processing method provided in the example embodiment of the disclosure, manual participation is not required, and a suspected malignant tumor may be rapidly and accurately positioned only using a neural network model obtained by deep learning training.

First, according to the example embodiment of the disclosure, deep learning training may be performed by using a large quantity of training samples to obtain a trained neural network model, so that the trained neural network model is used to accurately position the suspected malignant tumor. Samples for deep learning training may include: suspected malignant tumors as positive samples, and remaining obvious benign tumors, background regions and the like as negative samples.

Subsequently, the terminal positions the suspected malignant tumor by using the trained neural network model, and a specific process may be described as follows: The terminal photographs breast tissue to obtain a breast molybdenum target image; then, image preprocessing is performed on the breast molybdenum target image to remove noise and useless label background in the image and focus on a breast region that is used as a process object; next, candidate lump regions are extracted using an image segmentation technology; subsequently, the terminal determines, by using the neural network model obtained by deep learning training, whether a lump included in each candidate lump region is the suspected malignant tumor, for each candidate lump region one by one; if the terminal determines that there is a region including the suspected malignant tumor in the breast molybdenum target image, the terminal marks the region in the breast molybdenum target image, so that the suspected malignant tumor is rapidly and accurately positioned.

In an example application scenario, a neural network model obtained by deep learning training may be disposed on a cloud platform. When a suspected malignant tumor needs to be determined, the terminal may obtain a molybdenum target image, and then uploads the molybdenum target to the cloud platform. The cloud platform may screen out and position a suspected malignant tumor in the molybdenum target image by using the trained neural network model. If the cloud platform determines that there is a suspected malignant tumor in the molybdenum target image, the cloud platform marks a suspected malignant tumor region in the molybdenum target image, and then outputs the molybdenum target image with a suspected malignant tumor mark to the terminal.

By using the image processing method of the example embodiments of the disclosure, the suspected malignant tumor may be rapidly screened out and accurately positioned without manual participation, thereby greatly improving screening efficiency and positioning accuracy of the suspected malignant tumor.

The following describes in detail a specific technique of applying the disclosure to a technology of positioning a suspected malignant tumor in a breast molybdenum target image used in breast cancer detection.

The technology of positioning a suspected malignant tumor in a breast molybdenum target image is based on the latest computer vision technology and artificial intelligence technology, integrates and improves unsupervised segmentation and supervised classification methods, thereby improving a recall rate of the suspected malignant tumor and reducing a false alarm rate. The technology of positioning a suspected malignant tumor in a breast molybdenum target image may better serve breast cancer detection-related applications.

Figure 3:
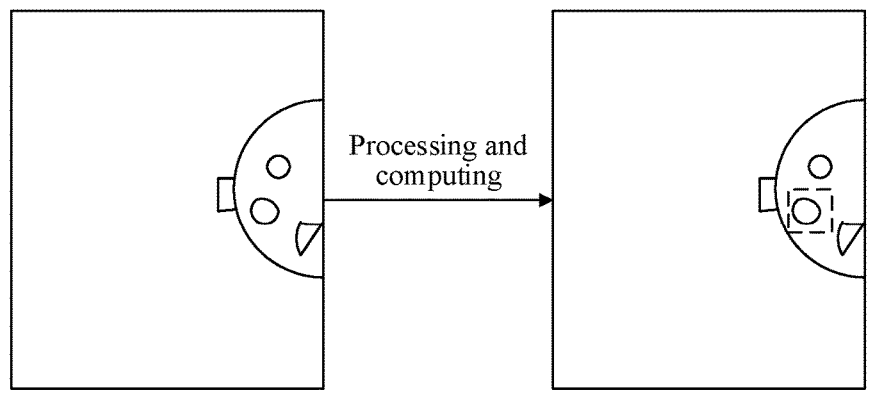
FIG. 3 is a schematic diagram of marking a molybdenum target image according to an optional example embodiment of the disclosure.

The suspected malignant tumor positioning technology may serve as a software interface. As shown in FIG. 3, a molybdenum target image is inputted, and the molybdenum target image includes three lump regions (this is merely an example, and does not constitute a specific limitation on the quantity of lump regions in the molybdenum target image).

After processing and calculation using the suspected malignant tumor positioning technology to which the example embodiments of the disclosure apply, the molybdenum target image with a suspected malignant tumor mark may be outputted, and one region in the three lump regions in the molybdenum target image is determined as a suspected malignant tumor region, which is the region with a broken line box shown in FIG. 3.

The suspected malignant tumor positioning technology according to example embodiments does not depend on a specific hardware environment.

In the technology for positioning a suspected malignant tumor according to example embodiments, the molybdenum target image is segmented mainly based on a genetic algorithm, and the suspected malignant tumor is screened out mainly based on a neural network model obtained by deep learning training from candidate regions obtained by segmenting the molybdenum target image. In deep learning, a large quantity of suspected malignant tumor samples and a large quantity of non-suspected malignant tumor samples are required for training.

Figure 4:
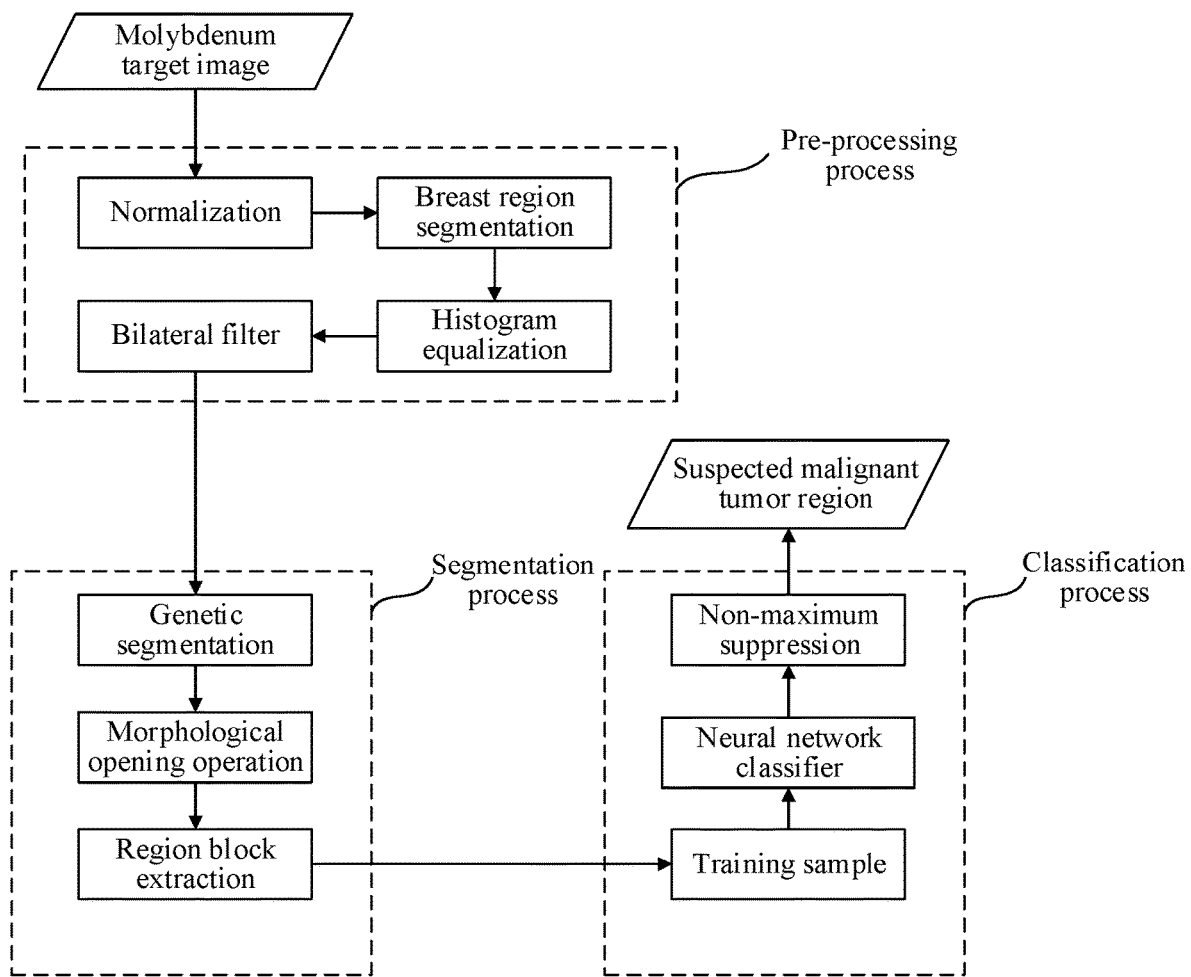
FIG. 4 is a schematic diagram of a positioning process of a suspected malignant tumor in a breast molybdenum target image according to an optional example embodiment of the disclosure.

In the technology for positioning a suspected malignant tumor according to example embodiments, a procedure of processing the inputted molybdenum target image, as shown in FIG. 4, mainly includes three processes: preprocessing, segmentation, and classification. The preprocessing process is mainly intended to remove noise and useless label background in the molybdenum target image and focus on a breast region that is used as a process object; the segmentation process is mainly intended to extract candidate regions; and in the classification process, each candidate region may be analyzed to determine whether a lump in the candidate region is a suspected malignant tumor. The following describes the three processes separately in detail:

(1) The preprocessing process may include the following processing operations:

Normalization: a gray range of the molybdenum target image is stretched to 0 to 255 through linear stretching, to improve robustness of subsequent processing.

Segmentation of a breast region: the breast region is extracted by using a morphological opening operation and binarization, and background such as a label is removed. The morphological opening operation may remove fine tissue and noise; binary classification may be performed in the segmentation process by using an Ostu's method, so that the breast region may be effectively extracted.

Histogram equalization: A subsequent segmentation algorithm is performed based on a molybdenum target image histogram. Therefore, it is desirable to improve the robustness of subsequent processing through histogram equalization.

Bilateral filter: The bilateral filter may be further used to remove noise that may exist in breast tissue, and regional homogeneity is improved to some extent. In addition, the bilateral filter does not destroy a segmentation edge.

(2) The segmentation process may include the following processing operations:

Genetic segmentation: Dimensions of the molybdenum target image may be reduced by using a 2D-wavelet transform (for example, a series is 3). For a low-detail image, statistics on the histogram of the molybdenum target image are collected after normalization, and image segmentation is performed based on the histogram. The histogram is segmented by using the genetic algorithm, a binary code form is used for a gene, and a length is equal to the quantity of gray scales. When a value of a bit in the binary code is 0, it indicates that the gray scale corresponding to the bit is a segmentation threshold. A value function of the genetic algorithm takes a maximum inter-class variance and a minimum intra-class variance as a standard. By using a general genetic algorithm procedure, three processes of iterative selection, crossover, and aberrance are repeated after population initialization, until convergence is achieved (e.g., the quantity of initial populations is 30, the quantity of iterations is 40, a selectivity is 10%, a crossing-over rate is 80%, and an aberration rate is 10%). Finally, a segmentation threshold is outputted, and the segmentation operation is performed on the original molybdenum target image according to the segmentation threshold.

Morphological opening operation: A morphological opening operation is performed on the image obtained by segmentation, to cut off a thymus connection or the like, thereby facilitating subsequent region extraction.

Region block extraction: For a segmentation result, regions with relatively high gray scales (for example, with gray scales ranked top 5) are first extracted as candidate regions. If the quantity of regions determined according to the order of gray scale does not meet a preset quantity, regions with relatively large areas may be further selected as the candidate regions according to the area of each region.

(3) The classification process may include the following processing operations:

Neural network model training and classification: Domestic hospital data may be used, and experts may label the data. Suspected malignant tumors are used as positive samples, and remaining obvious benign tumors and background regions are used as negative samples. Because the data is molybdenum target images, data enhancement of flipping and cropping is mainly performed, while data enhancement of color space is not required; in addition, the inputted malignant tumor sample needs to include an entire lump region and be surrounded by a small background region. After data enhancement, the samples are inputted as training data of the disclosure into an inception V3 model for training, and the quantity of output categories of the model is reset to 2. During weight initialization of the model, an ImageNet dataset is used first, then a public dataset DDSM is used, and finally the training data of the disclosure is used for transfer learning to obtain a final model weight (a descent algorithm uses RMSprop, a size of batch processing is 64, an initial learning rate is 0.01, and a maximum quantity of iterations is 100000). After the model training is completed, for any inputted candidate region, a probability of the candidate region being a suspected malignant tumor may be obtained through network computing. Generally, a candidate region is considered as a suspected malignant tumor when the probability is greater than 0.5.

Non-maximum suppression: For regions determined as suspected malignant tumor regions, a non-maximum suppression method is used to remove an overlapping region, where an overlapping degree threshold is set to 50% (which is merely an example herein, and no specific limitation is made). The main purpose is to reduce a false alarm rate while improving accuracy of positioning the suspected malignant tumor.

The segmentation method in the technology may also be replaced with a full convolutional neural network model, and GoogleNet used in the classification may also be replaced with other network models such as ResNet.

In the disclosure, based on the use of the segmentation method, simple morphological filter processing is performed on the regions obtained after segmentation, and then suspected malignant tumor classification is performed mainly depending on a classifier obtained by deep learning training. Accuracy of a result may be improved and full automation of the entire procedure is implemented.

According to the disclosure, a fusion method based on a tradition visual method and deep learning is first used in the field of lump detection, and an algorithm procedure is also first introduced (that is, has novelty over the conventional technologies). In addition, the use of deep learning may avoid manual screening, overcome a problem that design for irregular and complex features is difficult in a conventional method, and reduce sensitivity of the algorithm to post-segmentation processing. The disclosure has strong applicability, does not depend on a hardware environment, and may process molybdenum target pictures of various breast types.

According to another aspect of the example embodiments of the disclosure, a neural network model training method is further provided.

A trained neural network model may be obtained by performing deep learning training using the neural network model training method according to the example embodiment of the disclosure, and the trained neural network model may be applied to the image processing method according to the foregoing embodiment of the disclosure, so that a probability that a lump included in each candidate region is a target lump (that is, a suspected malignant tumor) is rapidly and accurately determined by using the trained neural network model, thereby rapidly and accurately positioning a suspected malignant tumor region in a molybdenum target image.

Figure 5:
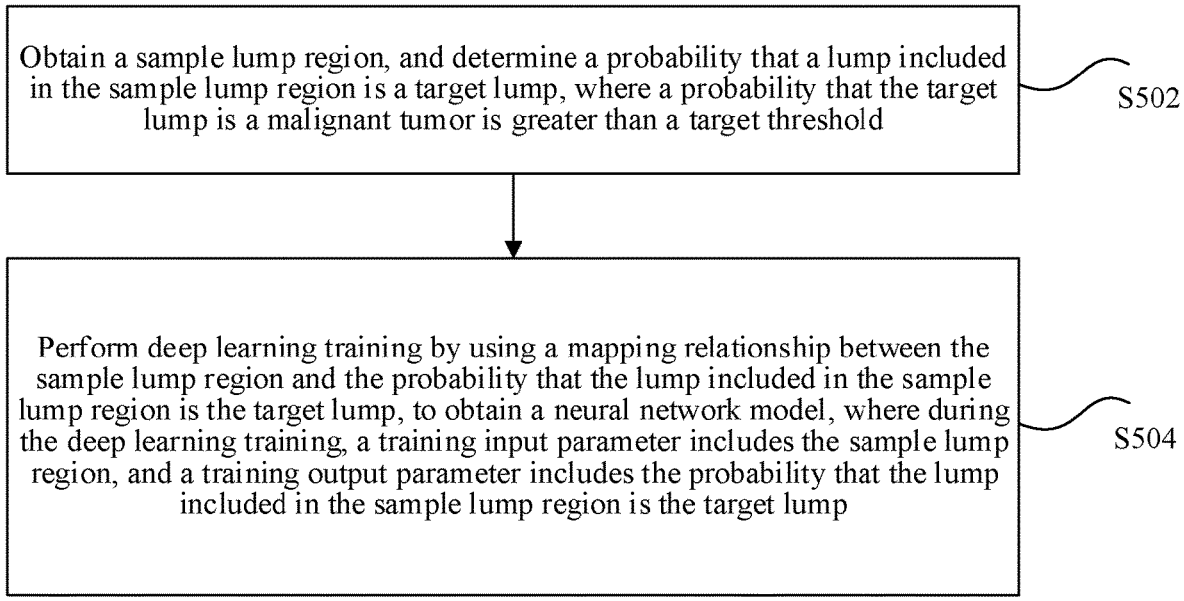
FIG. 5 is a flowchart of an optional neural network model training method according to an example embodiment of the disclosure.

FIG. 5 is a flowchart of an optional neural network model training method according to an example embodiment of the disclosure. As shown in FIG. 5, the neural network model training method may include the following operations:

Operation 502. A terminal obtains a sample lump region, and determines a probability that a lump included in the sample lump region is a target lump, where a probability that the target lump is a malignant tumor is greater than a target threshold.

Operation 504. The terminal performs deep learning training by using a mapping relationship between the sample lump region and the probability that the lump included in the sample lump region is the target lump, to obtain a neural network model, where during the deep learning training, a training input parameter includes the sample lump region, and a training output parameter includes the probability that the lump included in the sample lump region is the target lump.

Through operation S502 to operation S504, the neural network model may be obtained by deep learning training, and the trained neural network model may be used for indicating a mapping relationship between any lump region and a probability that a lump included in the lump region is a target lump. A probability that the target lump is a malignant tumor is greater than a target threshold. The target threshold may be set or adjusted according to actual requirements, and is not specifically limited herein. That is, the target lump in the sample lump region may be actually a suspected malignant tumor, and the trained neural network model may be used for indicating a mapping relationship between any lump region and a probability that a lump included in the lump region is the suspected malignant tumor.

Optionally, the sample lump region may include a first lump region and a second lump region. A lump included in the first lump region is the target lump, and a lump included in the second lump region is a non-target lump or the second lump region does not include a lump. Training samples include various types of lump regions, so that an effect of improving training accuracy of the neural network model may be achieved. When the deep learning training is performed, a larger quantity of sample lump regions indicates higher accuracy of the neural network model.

Optionally, after obtaining a sample lump region, the determining, by the terminal, a probability that a lump included in the sample lump region is a target lump may include: determining, by the terminal, the probability that the lump included in the sample lump region is the target lump from a database, where the database may pre-store the probability that the lump included in the sample lump region is the target lump. For example, the database may be a hospital database storing a large amount of medical data.

Optionally, the determining, by the terminal, a probability that a lump included in the sample lump region is a target lump may further include: determining, by the terminal according to an input parameter, the probability that the lump included in the sample lump region is the target lump, where the input parameter is used for indicating the probability that the lump included in the sample lump region is the target lump. For example, the input parameter may be the probability that the lump included in the sample lump region is the target lump determined by a doctor according to medical data and experience.

According to the example embodiment of the disclosure, the probability that the lump included in the sample lump region is the target lump may also be determined in any other manners, which are not individually illustrated herein.

After the terminal obtains the sample lump region and determines the probability that the lump included in the sample lump region is the target lump, according to the example embodiment of the disclosure, deep learning training may be performed on an untrained neural network model by using a mapping relationship between the sample lump region and the probability that the lump included in the sample lump region is the target lump. During training, a training input parameter may include the sample lump region, and a training output parameter may include the probability that the lump included in the sample lump region is the target lump.

Optionally, the performing, by the terminal, deep learning training by using a mapping relationship between the sample lump region and the probability that the lump included in the sample lump region is the target lump, to obtain a neural network model may include: performing, by the terminal, deep learning training by using a mapping relationship between the first lump region and the probability that the lump included in the first lump region is the target lump and a mapping relationship between the second lump region and the probability that the lump included in the second lump region is the target lump, to obtain the trained neural network model.

In an optional example, domestic hospital data may be used, and experts may label the data (e.g., more than 2200 pieces). Suspected malignant tumors are used as positive samples, and remaining obvious benign tumors and background regions are used as negative samples. Because the data is molybdenum target images, data enhancement of flipping and cropping is mainly performed, while data enhancement of color space is not required; in addition, the inputted malignant tumor sample needs to include an entire lump region and be surrounded by a small background region. After data enhancement, the samples are inputted as training data of the disclosure into an inception V3 model for training, and the quantity of output categories of the model is reset to 2. During weight initialization of the model, an ImageNet dataset is used first, then a public dataset DDSM is used, and finally the training data of the disclosure is used for transfer learning to obtain a final model weight. For example, a descent algorithm uses RMSprop, a size of batch processing is 64, an initial learning rate is 0.01, and a maximum quantity of iterations is 100000. After the model training is completed, for any inputted candidate region, a probability of the candidate region being a suspected malignant tumor may be obtained through calculation based on the trained neural network model. Generally, a candidate region is considered as a suspected malignant tumor when the probability is greater than 0.5.

When the terminal performs deep learning training by using sample lump regions, the sample lump regions may include the following types: a first lump region including the target lump, a second lump region including a non-target lump, and an image region without any lump, and the quantity of samples in each type is equivalent, so that accuracy of the neural network model obtained by deep learning training is improved.

According to another aspect of the example embodiments of the disclosure, a neural network model training device is further provided. The training device may be configured to perform the neural network model training method according to the example embodiment of the disclosure. The training device may obtain a trained neural network model by performing the neural network model training method according to the example embodiment of the disclosure, and the trained neural network model may be applied to the image processing method according to the foregoing embodiment of the disclosure, so that a probability that a lump included in each candidate region is a target lump (that is, a suspected malignant tumor) is rapidly and accurately determined by using the trained neural network model, thereby rapidly and accurately positioning a suspected malignant tumor region in a molybdenum target image.

The training device performs deep learning by executing the training method according to the foregoing embodiment of the disclosure, to obtain a neural network model. The probability that the lump included in each candidate region is the target lump may be accurately determined by using the trained neural network model. It is assumed that the probability threshold is 0.5. In this case, if it is determined, by using the neural network model obtained by deep learning training, that a probability of a lump included in a candidate region being the target lump is greater than 0.5, the candidate region may be determined as the target region, and the target region is marked in the molybdenum target image.

According to the example embodiment of the disclosure, by using the neural network model obtained by deep learning training, the target region including the target lump is determined from the plurality of candidate regions, and the suspected malignant tumor may be rapidly and accurately screened out and positioned without manual participation, thereby solving the technical problem in the related art that screening efficiency and positioning accuracy of the suspected malignant tumor are relatively low because the suspected malignant tumor in the molybdenum target image is positioned by manual screening, thereby implementing a technical effect of improving the screening efficiency and the positioning accuracy of the suspected malignant tumor.

To make the description simple, the foregoing method embodiments are stated as a series of action combinations. However, a person skilled in the art should understand that the disclosure is not limited to the described sequence of the actions because according to the disclosure, some operations may use another sequence or may be simultaneously performed. In addition, a person skilled in the art should also understand that the example embodiments described in the specification all belong to optional example embodiments, and the related actions and modules are not necessarily required in the disclosure.

According to the descriptions of the foregoing implementations, a person skilled in the art should clearly understand that the method according to the foregoing embodiments may be implemented by using software and a necessary universal hardware platform or by using hardware, but in many cases the former is a better implementation. Based on such an understanding, the technical solutions of the disclosure essentially or the part contributing to the related art may be implemented in a form of a software product. The computer software product is stored in a storage medium (such as a ROM/RAM, a magnetic disk, or an optical disc) and includes several instructions for instructing a terminal device (which may be a mobile phone, a computer, a server, a network device, or the like) to perform the methods described in the example embodiments of the disclosure.

According to another aspect of the example embodiments of the disclosure, an image processing apparatus configured to implement the foregoing image processing method is further provided. The image processing apparatus in an example embodiment may be disposed in a terminal that performs the image processing method according to the example embodiment of the disclosure.

Figure 6:
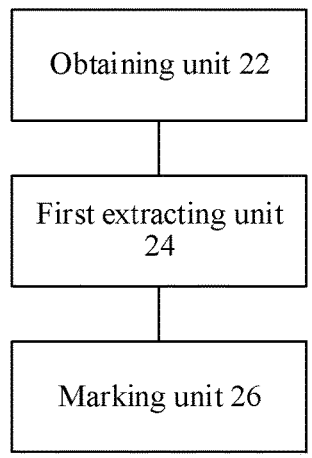
FIG. 6 is a schematic diagram of an optional image processing apparatus according to an example embodiment of the disclosure.

FIG. 6 is a schematic diagram of an optional image processing apparatus according to an example embodiment of the disclosure. As shown in FIG. 6, the apparatus may include:

an obtaining unit 22, configured to obtain a molybdenum target image; a first extracting unit 24, configured to extract a plurality of candidate regions from the molybdenum target image; and a marking unit 26, configured to mark, in the molybdenum target image, a target region in the plurality of candidate regions by using a neural network model obtained by deep learning training. The marking is based on a probability that a lump included in the target region is a target lump being greater than a first threshold, and a probability that the target lump is a malignant tumor being greater than a second threshold, and the neural network model is used for indicating a mapping relationship between the candidate region and a probability that a lump included in the candidate region is the target lump.

The obtaining unit 22 in an example embodiment may be configured to perform operation S202 in the example embodiment of the disclosure, the first extracting unit 24 in an example embodiment may be configured to perform operation S204 in the example embodiment of the disclosure, and the marking unit 26 in an example embodiment may be configured to perform operation S206 in the example embodiment of the disclosure.

Implemented examples and application scenarios of the foregoing modules are the same as those of the corresponding operations, but are not limited to the content disclosed in the foregoing embodiments. The foregoing modules may be run in the hardware environment shown in FIG. 1 as a part of the apparatus, and may be implemented by software, or may be implemented by hardware.

Figure 7:
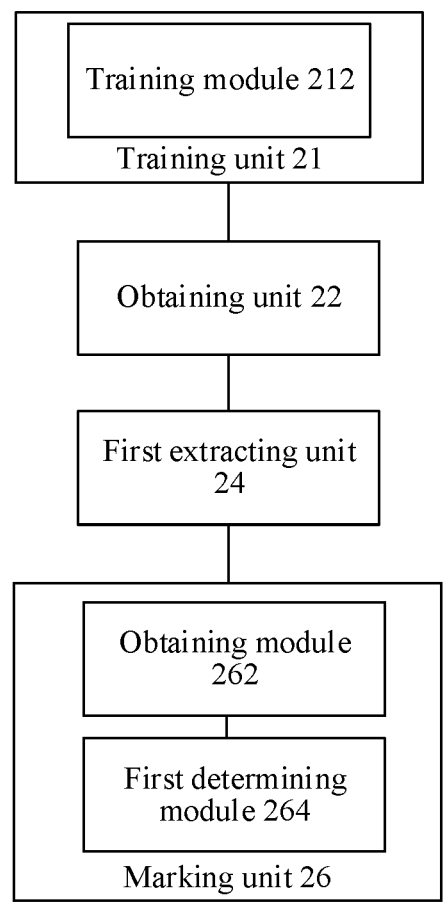
FIG. 7 is a schematic diagram of another optional image processing apparatus according to an example embodiment of the disclosure.

Optionally, as shown in FIG. 7, the marking unit 26 may include: an obtaining module 262, configured to obtain, by using the neural network model, a probability that a lump included in each candidate region in the plurality of candidate regions is the target lump, and a first determining module 264, configured to determine a candidate region whose probability is greater than the first threshold as the target region and mark the target region in the molybdenum target image.

Optionally, as shown in FIG. 7, the image processing apparatus may further include: a training unit 21, configured to perform, before the molybdenum target image is obtained, deep learning training by using a mapping relationship between a sample lump region and a probability that a lump included in the sample lump region is the target lump, to obtain the neural network model, where during the deep learning training, a training input parameter includes the sample lump region, and a training output parameter includes the probability that the lump included in the sample lump region is the target lump.

Optionally, the sample lump region may include a first lump region and a second lump region, a lump included in the first lump region is the target lump, and a lump included in the second lump region is a non-target lump or the second lump region does not include a lump. As shown in FIG. 7, the training unit 21 may include: a training module 212, configured to perform deep learning training by using a mapping relationship between the first lump region and a probability that the lump included in the first lump region is the target lump and a mapping relationship between the second lump region and a probability that the lump included in the second lump region is the target lump, to obtain the neural network model.

Figure 8:
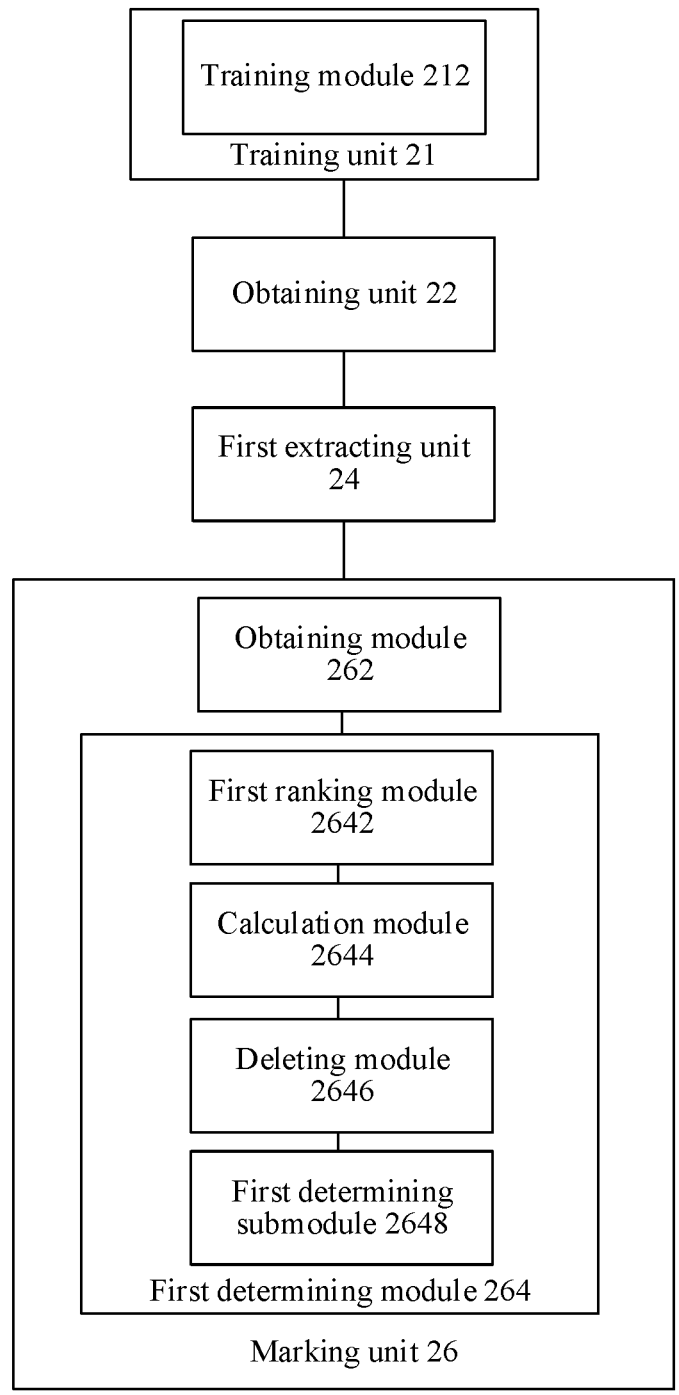
FIG. 8 is a schematic diagram of another optional image processing apparatus according to an example embodiment of the disclosure.

Optionally, as shown in FIG. 8, in a case that there is a plurality of candidate regions whose probabilities of including a target lump are greater than the first threshold, the first determining module 264 may include: a first ranking module 2642, configured to rank, according to values of the probabilities, the plurality of candidate regions whose probabilities of including a target lump are greater than the first threshold; a calculation module 2644, configured to calculate an overlapping area between a first candidate region and each second candidate region separately, where the first candidate region is a candidate region with the largest probability in the plurality of candidate regions whose probabilities of including a target lump are greater than the first threshold, and the second candidate region is a candidate region other than the first candidate region in the plurality of candidate regions whose probabilities of including a target lump are greater than the first threshold; a deleting module 2646, configured to delete any second candidate region whose overlapping area with the first candidate region is greater than a third threshold from the plurality of candidate regions whose probabilities of including a target lump are greater than the first threshold, to obtain a remaining candidate region; and a first determining submodule 2648, configured to determine the remaining candidate region as the target region.

Figure 9:
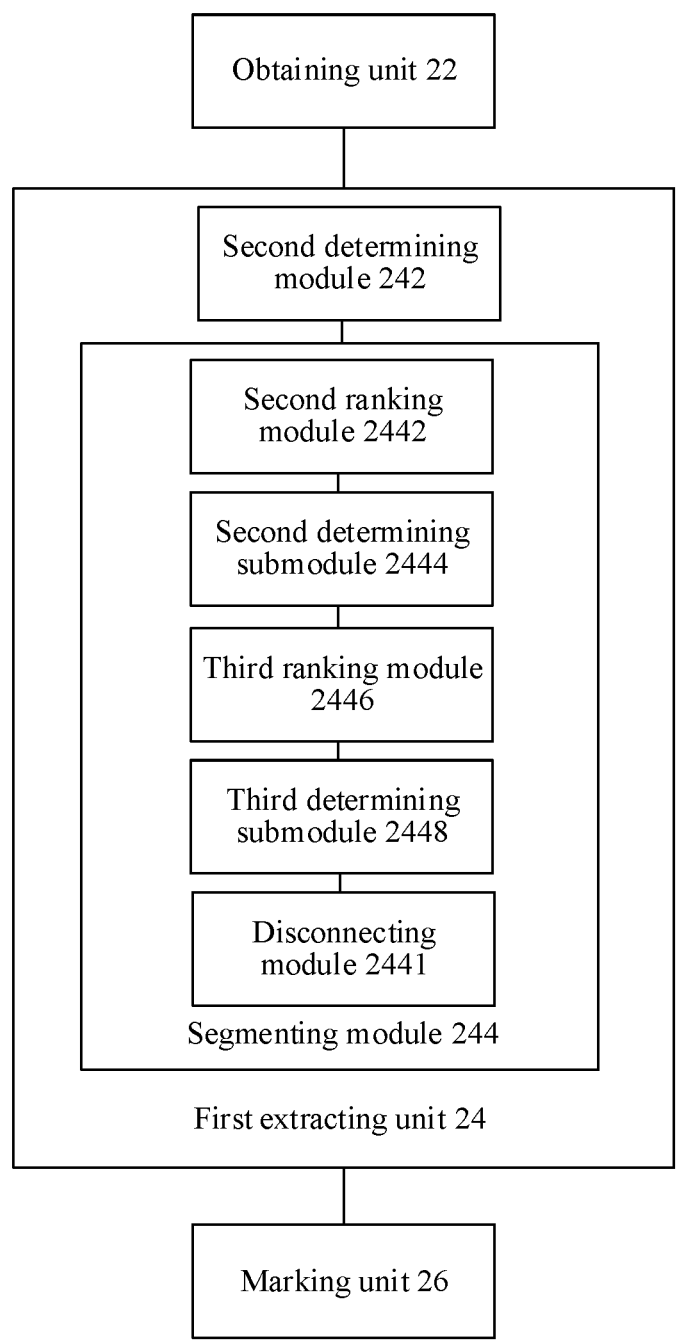
FIG. 9 is a schematic diagram of another optional image processing apparatus according to an example embodiment of the disclosure.

Optionally, as shown in FIG. 9, the first extracting unit 24 may include: a second determining module 242, configured to determine an image segmentation threshold, and a segmentation module 244, configured to segment the molybdenum target image according to the image segmentation threshold, to obtain the plurality of candidate regions.

Optionally, as shown in FIG. 9, the segmentation module 244 may include: a second ranking module 2442, configured to rank, according to gray scales, a plurality of image regions obtained by segmenting the molybdenum target image according to the image segmentation threshold, where the gray scales are related to the image segmentation threshold; and a second determining submodule 2444, configured to determine image regions whose ranks are equal to or are higher than a fourth threshold in the plurality of image regions as the candidate regions.

Optionally, as shown in FIG. 9, in a case that a quantity of image regions whose ranks are equal to or are higher than the fourth threshold in the plurality of image regions is greater than a fifth threshold, the segmentation module 244 may include: a third ranking module 2446, configured to rank, according to areas of the image regions, the image regions whose ranks are equal to or are higher than the fourth threshold in the plurality of image regions; and a third determining submodule 2448, configured to determine image regions whose areas are greater than a sixth threshold, among the image regions whose ranks are equal to or are higher than the fourth threshold in the plurality of image regions, as the candidate regions, where a quantity of determined image regions whose areas are greater than the sixth threshold is equal to the fifth threshold, among the image regions whose ranks are equal to or higher than the fourth threshold in the plurality of image regions.

Optionally, as shown in FIG. 9, the segmentation module 244 may include: a disconnecting module 2441, configured to disconnect a connection line that is used for indicating a tissue connection of a human body part in each image region in the plurality of image regions, to obtain the plurality of candidate regions.

Figure 10:
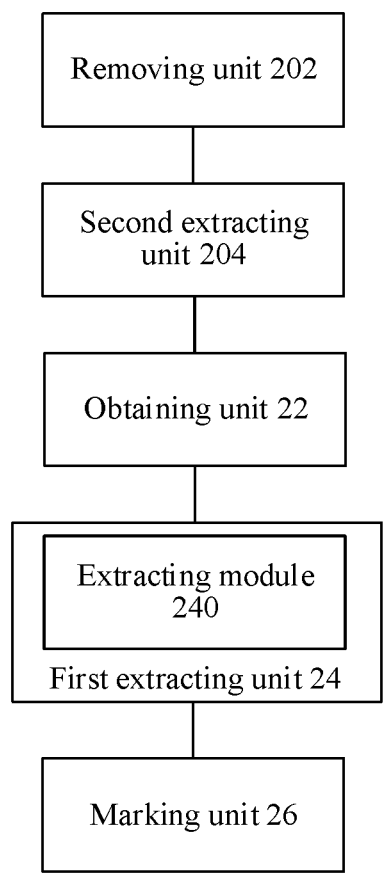
FIG. 10 is a schematic diagram of another optional image processing apparatus according to an example embodiment of the disclosure.

Optionally, as shown in FIG. 10, the image processing apparatus may further include: a removing unit 202, configured to: after the molybdenum target image is obtained, remove noise in the molybdenum target image, to obtain a denoised molybdenum target image; a second extracting unit 204, configured to extract a target image from the denoised molybdenum target image, where the target image is an image including a human body part. The first extracting unit 24 may include: an extracting module 240, configured to extract the plurality of candidate regions from the target image.

Optionally, the molybdenum target image in the image processing apparatus may be a breast molybdenum target image.

Implemented examples and application scenarios of the foregoing modules are the same as those of the corresponding operations, but are not limited to the content disclosed in the foregoing embodiments. The foregoing modules may be run in the hardware environment shown in FIG. 1 as a part of the apparatus, and may be implemented by software, or may be implemented by hardware.

The foregoing modules may solve the technical problem in the related art that screening efficiency and positioning accuracy of a suspected malignant tumor are relatively low because the suspected malignant tumor in the molybdenum target image is positioned by manual screening.

According to still another aspect of the example embodiments of the disclosure, an electronic apparatus for implementing the foregoing image processing method and neural network model training method is further provided.

Figure 11:
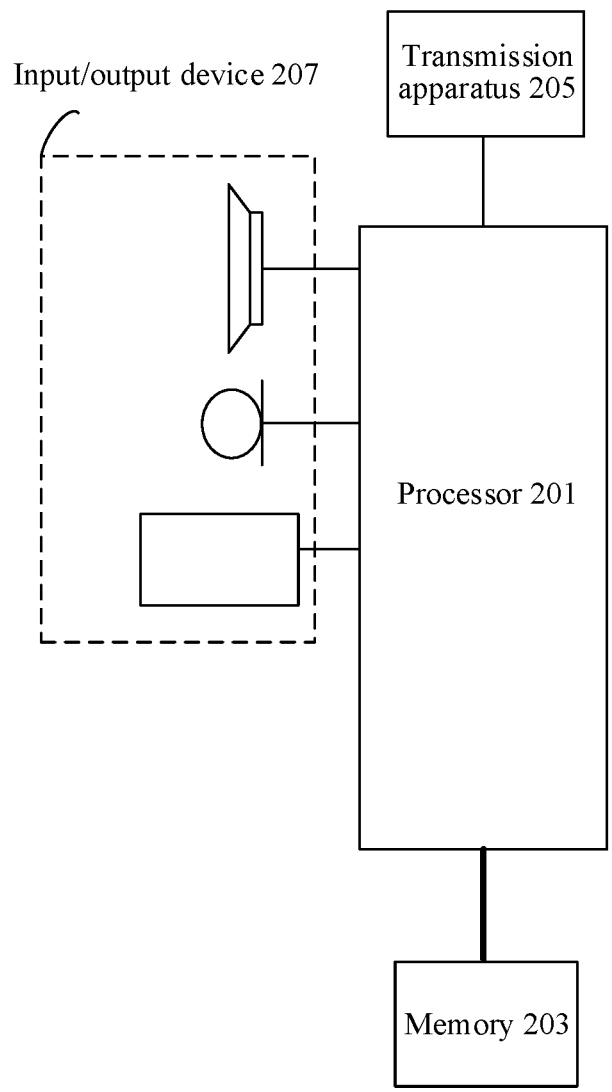
FIG. 11 is a structural block diagram of an electronic apparatus according to an example embodiment of the disclosure.

FIG. 11 is a structural block diagram of an electronic apparatus according to an example embodiment of the disclosure. As shown in FIG. 11, the electronic apparatus may include: one or more (only one is shown in the figure for illustrative purposes) processors 201 and a memory 203. The memory 203 may store a computer program, and the processor 201 may be configured to run the computer program to perform the image processing method and the neural network model training method according to the example embodiments of the disclosure.

The memory 203 may be configured to store the computer program and a module, for example, a program instruction/module corresponding to the image processing method and apparatus and the neural network model training method and device in the example embodiments of the disclosure. The processor 201 runs the computer program and module stored in the memory 203, to implement various functional applications and data processing, that is, implement the foregoing image processing method and the neural network model training method. The memory 203 may include a high-speed random access memory, and may further include a non-volatile memory, for example, one or more magnetic storage apparatuses, flash memories, or other non-volatile solid-state memories. In some examples, the memory 203 may further include memories remotely disposed relative to the processor 201, and these remote memories may be connected to a terminal through a network. Examples of the network include, but are not limited to, the Internet, an intranet, a local area network, a mobile communications network, and a combination thereof.

Optionally, as shown in FIG. 11, the electronic apparatus may further include a transmission apparatus 205 and an input/output device 207. The transmission apparatus 205 is configured to receive or transmit data through a network. Specific examples of the network may include a wired network and a wireless network. In an example, the transmission apparatus 205 includes a network interface controller (NIC), and the network interface controller may be connected to another network device or a router by using a network cable, so as to communicate with the Internet or a local area network. In an example, the transmission apparatus 205 is a radio frequency (RF) module, and the radio frequency module is configured to communicate with the Internet in a wireless manner.

A person of ordinary skill in the art should understand that, the structure shown in FIG. 11 is only illustrative. The electronic apparatus may be a terminal device such as a smartphone (for example, an Android mobile phone, or an iOS mobile phone), a tablet computer, a palmtop computer, a mobile Internet device (MID), or a portable Android device (PAD). FIG. 11 does not constitute a limitation on a structure of the foregoing electronic apparatus. For example, the electronic apparatus may further include more or fewer components (for example, a network interface and a display apparatus) than those shown in FIG. 11, or has a configuration different from that shown in FIG. 11.

Optionally, in an example embodiment, the memory 203 may be configured to store the computer program.

Optionally, in an example embodiment, the processor may be configured to run the computer program to perform the following operations: obtaining a molybdenum target image; extracting a plurality of candidate regions from the molybdenum target image; and marking, in the molybdenum target image, a target region in the plurality of candidate regions by using a neural network model obtained by deep learning training, where a probability that a lump included in the target region is a target lump is greater than a first threshold, a probability that the target lump is a malignant tumor is greater than a second threshold, and the neural network model is used for indicating a mapping relationship between the candidate region and a probability that a lump included in the candidate region is the target lump.

The processor 201 may be further configured to perform the following operations: obtaining, by using the neural network model, a probability that a lump included in each candidate region in the plurality of candidate regions is the target lump; and determining a candidate region whose probability is greater than the first threshold as the target region, and marking the target region in the molybdenum target image.

The processor 201 may be further configured to perform the following operations: performing, before obtaining the molybdenum target image, deep learning training by using a mapping relationship between a sample lump region and a probability that a lump included in the sample lump region is the target lump, to obtain the neural network model, where during the deep learning training, a training input parameter includes the sample lump region, and a training output parameter includes the probability that the lump included in the sample lump region is the target lump.

The processor 201 may be further configured to perform the following operations: performing deep learning training by using a mapping relationship between a first lump region and a probability that a lump included in the first lump region is the target lump and a mapping relationship between a second lump region and a probability that a lump included in the second lump region is the target lump, to obtain the neural network model, where the sample lump region includes the first lump region and the second lump region, the lump included in the first lump region is the target lump, and the lump included in the second lump region is a non-target lump or the second lump region does not include a lump.

The processor 201 may be further configured to perform the following operations: in a case that there are a plurality of candidate regions whose probabilities of including a target lump are greater than the first threshold, ranking, according to values of the probabilities, the plurality of candidate regions whose probabilities of including a target lump are greater than the first threshold; calculating an overlapping area between a first candidate region and each second candidate region separately, where the first candidate region is a candidate region with the largest probability in the plurality of candidate regions whose probabilities of including a target lump are greater than the first threshold, and the second candidate region is a candidate region other than the first candidate region in the plurality of candidate regions whose probabilities of including a target lump are greater than the first threshold; deleting any second candidate region whose overlapping area with the first candidate region is greater than a third threshold from the plurality of candidate regions whose probabilities of including a target lump are greater than the first threshold, to obtain a remaining candidate region; and determining the remaining candidate region as the target region.

The processor 201 is further configured to perform the following operations: determining an image segmentation threshold; and segmenting the molybdenum target image according to the image segmentation threshold, to obtain the plurality of candidate regions.

The processor 201 is further configured to perform the following operations: ranking, according to gray scales, a plurality of image regions obtained by segmenting the molybdenum target image according to the image segmentation threshold, where the gray scales are related to the image segmentation threshold; and determining image regions whose ranks are equal to or higher than a fourth threshold in the plurality of image regions as the candidate regions.

The processor 201 is further configured to perform the following operations: in a case that a quantity of image regions whose ranks are equal to or higher than the fourth threshold in the plurality of image regions is greater than a fifth threshold, ranking, according to areas of the image regions, the image regions whose ranks are equal to or higher than the fourth threshold in the plurality of image regions; and determining image regions whose areas are greater than a sixth threshold in the image regions whose ranks are equal to or higher than the fourth threshold in the plurality of image regions as the candidate regions, where a quantity of the determined image regions whose areas are greater than the sixth threshold is equal to a fifth threshold, among the image regions whose ranks are equal to or higher than the fourth threshold in the plurality of image regions.

The processor 201 is further configured to perform the following operations: disconnecting a connection line that is used for indicating a tissue connection of a human body part in each image region in the plurality of image regions obtained by segmenting the molybdenum target image according to the image segmentation threshold, to obtain the plurality of candidate regions.

The processor 201 is further configured to perform the following operations: after obtaining the molybdenum target image, removing noise in the molybdenum target image, to obtain a denoised molybdenum target image; extracting a target image from the denoised molybdenum target image, where the target image is an image including a human body part; and extracting the plurality of candidate regions from the target image.

The processor 201 is further configured to perform the following operations: obtaining a sample lump region, and determining a probability that a lump included in the sample lump region is the target lump, where the probability that the target lump is a malignant tumor is greater than a target threshold; and performing deep learning training by using a mapping relationship between the sample lump region and the probability that the lump included in the sample lump region is the target lump, to obtain the neural network model, where during the deep learning training, a training input parameter includes the sample lump region, a training output parameter includes the probability that the lump included in the sample lump region is the target lump.

The processor 201 may be further configured to perform the following operations: performing deep learning training by using a mapping relationship between a first lump region and a probability that a lump included in the first lump region is the target lump and a mapping relationship between a second lump region and a probability that a lump included in the second lump region is the target lump, to obtain the neural network model, where the sample lump region includes the first lump region and the second lump region, the lump included in the first lump region is the target lump, and the lump included in the second lump region is a non-target lump or the second lump region does not include a lump.

The processor 201 is further configured to perform the following operations: determining the probability that the lump included in the sample lump region is the target lump from a database, where the database pre-stores the probability that the lump included in the sample lump region is the target lump; or determining, according to an input parameter, the probability that the lump included in the sample lump region is the target lump, where the input parameter is used for indicating the probability that the lump included in the sample lump region is the target lump.

Optionally, for a specific example in an example embodiment, refer to the examples described in the foregoing embodiments, and details are not described herein again in an example embodiment.

By using an example embodiment of the disclosure, an image processing solution is provided. A molybdenum target image is obtained, a plurality of candidate regions is extracted from the molybdenum target image, and a target region in the plurality of candidate regions is marked in the molybdenum target image by using a neural network model obtained by deep learning training. A probability that a lump included in the target region is a target lump is greater than a first threshold, a probability that the target lump is a malignant tumor is greater than a second threshold, and the neural network model is used for indicating a mapping relationship between the candidate region and a probability that a lump included in the candidate region is the target lump. A suspected malignant tumor region is automatically marked in the molybdenum target image without manual participation, thereby solving the technical problem in the related art that screening efficiency and positioning accuracy of a suspected malignant tumor are relatively low because the suspected malignant tumor in the molybdenum target image is positioned by manual screening, and achieving a technical effect of improving the screening efficiency and the positioning accuracy of the suspected malignant tumor.

According to still another aspect of the example embodiments of the disclosure, a storage medium is further provided. The storage medium stores a computer program. The computer program is configured to perform, during running, the operations of the image processing method and the operations of the neural network model training method in the foregoing embodiments.

Optionally, in an example embodiment, the storage medium may be located in at least one of a plurality of network devices on a network shown in the foregoing embodiments.

Optionally, in an example embodiment, the storage medium is configured to store the computer program for performing the following operations:

S1. Obtain a molybdenum target image.

S2. Extract a plurality of candidate regions from the molybdenum target image.

S3. Mark, by using a neural network model obtained by deep learning training, a target region in the plurality of candidate regions in the molybdenum target image, where a probability that a lump included in the target region is a target lump is greater than a first threshold, a probability that the target lump is a malignant tumor is greater than a second threshold, and the neural network model is used for indicating a mapping relationship between the candidate region and a probability that a lump included in the candidate region is the target lump.

Optionally, the storage medium is further configured to store the computer program for performing the following operations: obtaining, by using the neural network model, a probability that a lump included in each candidate region in the plurality of candidate regions is the target lump; and determining a candidate region whose probability is greater than the first threshold as the target region, and marking the target region in the molybdenum target image.

Optionally, the storage medium is further configured to store the computer program for performing the following operations: before obtaining the molybdenum target image, performing deep learning training by using a mapping relationship between a sample lump region and a probability that a lump included in the sample lump region is the target lump, to obtain the neural network model, where during classification training, a training input parameter includes the sample lump region, and a training output parameter includes the probability that the lump included in the sample lump region is the target lump.

Optionally, the storage medium is further configured to store the computer program for performing the following operations: performing deep learning training by using a mapping relationship between a first lump region and a probability that a lump included in the first lump region is the target lump and a mapping relationship between a second lump region and a probability that a lump included in the second lump region is the target lump, to obtain the neural network model, where the sample lump region includes the first lump region and the second lump region, the lump included in the first lump region is the target lump, and the lump included in the second lump region is a non-target lump or the second lump region does not include a lump (that is, the second lump region does not include the target lump).

Optionally, the storage medium is further configured to store the computer program for performing the following operations: in a case that there is a plurality of candidate regions whose probabilities of including a target lump are greater than the first threshold, ranking, according to values of the probabilities, the plurality of candidate regions whose probabilities of including a target lump are greater than the first threshold; calculating an overlapping area between a first candidate region and each second candidate region separately, where the first candidate region is a candidate region with the largest probability in the plurality of candidate regions whose probabilities of including a target lump are greater than the first threshold, and the second candidate region is a candidate region other than the first candidate region in the plurality of candidate regions whose probabilities of including a target lump are greater than the first threshold; deleting any second candidate region whose overlapping area with the first candidate region is greater than a third threshold from the plurality of candidate regions whose probabilities of including a target lump are greater than the first threshold, to obtain a remaining candidate region; and determining the remaining candidate region as the target region.

Optionally, the storage medium is further configured to store the computer program for performing the following operations: determining an image segmentation threshold; and segmenting the molybdenum target image according to the image segmentation threshold, to obtain the plurality of candidate regions.

Optionally, the storage medium is further configured to store the computer program for performing the following operations: ranking, according to gray scales, a plurality of image regions obtained by segmenting the molybdenum target image according to the image segmentation threshold, where the gray scales are related to the image segmentation threshold; and determining image regions whose ranks are equal to or higher than a fourth threshold in the plurality of image regions as the candidate regions.

Optionally, the storage medium is further configured to store the computer program for performing the following operations: in a case that a quantity of image regions whose ranks are equal to or are higher than the fourth threshold in the plurality of image regions is greater than a fifth threshold, ranking, according to areas of the image regions, the image regions whose ranks are equal to or higher than the fourth threshold in the plurality of image regions; and determining image regions whose areas are greater than a sixth threshold in the image regions whose ranks are equal to or higher than the fourth threshold in the plurality of image regions as the candidate regions, where a quantity of the determined image regions whose areas are greater than the sixth threshold is equal to a fifth threshold, among the image regions ranks are equal to or are higher than the fourth threshold in the plurality of image regions.

Optionally, the storage medium is further configured to store the computer program for performing the following operation: disconnecting a connection line that is used for indicating a tissue connection of a human body part in each image region in a plurality of image regions obtained by segmenting the molybdenum target image according to the image segmentation threshold, to obtain the plurality of candidate regions.

Optionally, the storage medium is further configured to store the computer program for performing the following operations: after obtaining the molybdenum target image, removing noise in the molybdenum target image, to obtain a denoised molybdenum target image; extracting a target image from the denoised molybdenum target image, where the target image is an image including a human body part; and extracting the plurality of candidate regions from the target image.

Optionally, the storage medium is further configured to store the computer program for performing the following operations: obtaining a sample lump region, and determining a probability that a lump included in the sample lump region is a target lump, where a probability that the target lump is a malignant tumor is greater than a target threshold; performing deep learning training by using a mapping relationship between the sample lump region and the probability that the lump included in the sample lump region is the target lump, to obtain the neural network model, where during the deep learning training, a training input parameter includes the sample lump region, and a training output parameter includes the probability that the lump included in the sample lump region is the target lump.

Optionally, the storage medium is further configured to store the computer program for performing the following operations: performing deep learning training by using a mapping relationship between a first lump region and a probability that a lump included in the first lump region is the target lump and a mapping relationship between a second lump region and a probability that a lump included in the second lump region is the target lump, to obtain the neural network model. The sample lump region includes the first lump region and the second lump region, the lump included in the first lump region is the target lump, and the lump included in the second lump region is a non-target lump or the second lump region does not include a lump.

Optionally, the storage medium is further configured to store the computer program for performing the following operations: determining the probability that the lump included in the sample lump region is the target lump from a database, where the database pre-stores the probability that the lump included in the sample lump region is the target lump, or determining, according to an input parameter, the probability that the lump included in the sample lump region is the target lump, where the input parameter is used for indicating the probability that the lump included in the sample lump region is the target lump.

Optionally, for a specific example in an example embodiment, refer to the examples described in the foregoing embodiments, and details are not described herein again in an example embodiment.

A person of ordinary skill in the art should understand that all or some of the operations of the methods in the foregoing embodiments may be implemented by a program instructing relevant hardware of the terminal device. The program may be stored in a computer-readable storage medium. The storage medium may include a flash disk, a read only memory (ROM), a random access memory (RAM), a magnetic disk, an optical disc, and the like.

The sequence numbers of the foregoing embodiments of the disclosure are merely for the convenience of description, and do not imply the preference among the example embodiments.

In a case that the integrated unit in the foregoing embodiments is implemented in the form of a software functional unit and sold or used as an independent product, the integrated unit may be stored in the foregoing computer-readable storage medium. Based on such understanding, the technical solutions of the disclosure essentially, or the part contributing to the related art, or all or some of the technical solutions may be implemented in a form of a software product. The computer software product is stored in a storage medium and includes several instructions for instructing one or more computer devices (which may be a PC, a server, a network device, or the like) to perform all or some of operations of the methods in the example embodiments of the disclosure.

In the foregoing embodiments of the disclosure, descriptions of the example embodiments have different emphases, and as for parts that are not described in detail in one embodiment, reference may be made to the relevant descriptions of the other embodiments.

In the several embodiments provided in the disclosure, it is to be understood that the disclosed client may be implemented in other manners. The apparatus embodiments described above are merely examples. For example, the division of the units is merely the division of logic functions, and may use other division manners during actual implementation. For example, a plurality of units or components may be combined, or may be integrated into another system, or some features may be omitted or not performed. In addition, the displayed or discussed mutual couplings or direct couplings or communication connections may be implemented through some interfaces. The indirect couplings or communication connections between the units or modules may be implemented in an electronic form or another form.

The units described as separate parts may or may not be physically separate, and parts displayed as units may or may not be physical units, may be located in one position, or may be distributed on a plurality of network units. Some or all of the units may be selected according to actual requirements to achieve the objectives of the solutions in the example embodiments.

In addition, functional units in the example embodiments of the disclosure may be integrated into one processing unit, or each of the units may exist alone physically, or two or more units are integrated into one unit. The integrated unit may be implemented in the form of hardware, or may be implemented in the form of a software functional unit.

The above descriptions are merely optional implementations of the disclosure, and a person of ordinary skill in the art may make various improvements and refinements without departing from the spirit of the disclosure. All such modifications and refinements are also considered as the protection scope of the disclosure.

INDUSTRIAL APPLICABILITY

In the example embodiments of the disclosure, a molybdenum target image is obtained, a plurality of candidate regions is extracted from the molybdenum target image, and a target region in the plurality of candidate regions is marked in the molybdenum target image by using a neural network model obtained by deep learning training. A probability that a lump included in the target region is a target lump is greater than a first threshold, a probability that the target lump is a malignant tumor is greater than a second threshold, and the neural network model is used for indicating a mapping relationship between the candidate region and a probability that a lump included in the candidate region is the target lump. A target lump region is automatically marked in the molybdenum target image without manual participation, thereby solving the technical problem in the related art that screening efficiency and positioning accuracy of a suspected malignant tumor are relatively low because the suspected malignant tumor in the molybdenum target image is positioned by manual screening, and achieving a technical effect of improving the screening efficiency and the positioning accuracy of the suspected malignant tumor.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

The foregoing example embodiments only describe several implementations of the disclosure, which are described specifically and in detail, and therefore cannot be construed as a limitation to the patent scope of the disclosure. A person of ordinary skill in the art may make various changes and improvements without departing from the ideas of the disclosure, which shall all fall within the protection scope of the disclosure. Therefore, the protection scope of the patent of the disclosure shall be subject to the appended claims.

What is claimed is:

1. An image processing method performed by a terminal, the method comprising:
   obtaining a molybdenum target image;
   extracting a plurality of candidate regions from the molybdenum target image; and
   marking, in the molybdenum target image, a target region in the plurality of candidate regions by using a neural network model obtained by deep learning training,
   wherein a probability that a lump comprised in the target region is a target lump is greater than a first threshold, a probability that the target lump is a malignant tumor is greater than a second threshold, and the neural network model is used for indicating a mapping relationship between a candidate region and a probability that a lump comprised in the candidate region is the target lump.

2. The method according to claim 1, wherein the marking comprises:
   obtaining, by using the neural network model, a probability that a lump comprised in each candidate region in the plurality of candidate regions is the target lump; and
   determining a candidate region whose probability is greater than the first threshold as the target region, and marking the target region in the molybdenum target image.

3. The method according to claim 2, wherein, based on a plurality of candidate regions having probabilities of including the target lump that are greater than the first threshold, the determining the candidate region comprises:
   ranking, according to values of the probabilities, the plurality of candidate regions whose probabilities of including the target lump that are greater than the first threshold;
   calculating an overlapping area between a first candidate region and each second candidate region respectively, the first candidate region being a candidate region having a largest probability of including the target lump among the plurality of candidate regions whose probabilities of including the target lump that are greater than the first threshold, and the second candidate region being a candidate region other than the first candidate region in the plurality of candidate regions whose probabilities of including the target lump that are greater than the first threshold;
   deleting any second candidate region whose overlapping area with the first candidate region is greater than a third threshold from the plurality of candidate regions whose probabilities of including the target lump that are greater than the first threshold, to obtain at least one remaining candidate region; and
   determining the at least one remaining candidate region as the target region.

4. The method according to claim 1, further comprising, prior to the obtaining the molybdenum target image:
   performing deep learning training by using a mapping relationship between a sample lump region and a probability that a lump comprised in the sample lump region is the target lump, to obtain the neural network model, wherein, during the deep learning training, a training input parameter comprises the sample lump region, and a training output parameter comprises the probability that the lump comprised in the sample lump region is the target lump.

5. The method according to claim 4, wherein the sample lump region comprises a first lump region and a second lump region, the first lump region comprises the target lump and the second lump region does not comprise the target lump, and
   the performing the deep learning training comprises:
   performing deep learning training by using a mapping relationship between the first lump region and a probability that the lump comprised in the first lump region is the target lump and a mapping relationship between the second lump region and a probability that the lump comprised in the second lump region is the target lump, to obtain the neural network model.

6. The method according to claim 1, wherein the extracting comprises:
   determining at least one image segmentation threshold; and
   segmenting the molybdenum target image according to the at least one image segmentation threshold, to obtain the plurality of candidate regions.

7. The method according to claim 6, wherein the segmenting comprises:
   ranking, according to gray scales in comparison with the at least one image segmentation threshold, a plurality of image regions obtained by segmenting the molybdenum target image; and
   determining, as the plurality of candidate regions, image regions whose ranks are equal to or greater than a fourth threshold in the plurality of image regions.

8. The method according to claim 7, wherein, based on a quantity of the image regions whose ranks are equal to or higher than the fourth threshold in the plurality of image regions being greater than a fifth threshold, the segmenting comprises:
   determining, as the plurality of candidate regions, image regions whose areas are greater than a sixth threshold, among the image regions whose ranks are equal to or higher than the fourth threshold in the plurality of image regions, a quantity of the determined image regions whose areas are greater than the sixth threshold being equal to the fifth threshold.

9. The method according to claim 6, wherein the segmenting comprises:
   disconnecting a connection line that is used for indicating a tissue connection of a human body part in each image region in the plurality of candidate regions obtained by segmenting the molybdenum target image according to the at least one image segmentation threshold.

10. The method according to claim 6, wherein the neural network model is obtained based on a neural network model training method, comprising:
    obtaining a sample lump region, and determining a probability that a lump comprised in the sample lump region is a target lump, a probability that the target lump is the malignant tumor being greater than a target threshold; and
    performing deep learning training by using a mapping relationship between the sample lump region and the probability that the lump comprised in the sample lump region is the target lump, to obtain the neural network model, wherein, during the deep learning training, a training input parameter comprises the sample lump region, and a training output parameter comprises the probability that the lump comprised in the sample lump region is the target lump.

11. The method according to claim 10, wherein the sample lump region comprises a first lump region comprising the target lump and a second lump region not comprising the target lump, and the performing the deep learning training comprises:
    performing the deep learning training by using a mapping relationship between the first lump region and a probability that the lump comprised in the first lump region is the target lump and a mapping relationship between the second lump region and a probability that the lump comprised in the second lump region is the target lump, to obtain the neural network model.

12. The method according to claim 10, the determining the probability that the lump comprised in the sample lump region is the target lump comprises:
    determining the probability that the lump comprised in the sample lump region is the target lump from a database, the database pre-storing the probability that the lump comprised in the sample lump region is the target lump; or
    determining, according to an input parameter, the probability that the lump comprised in the sample lump region is the target lump.

13. An electronic apparatus, comprising at least one memory and at least one processor, the at least one memory storing a computer program, and the at least one processor being configured to execute the computer program to perform the method according to claim 10.

14. An image processing apparatus, the apparatus being installed in a terminal comprising at least one memory and at least one processor, the terminal being configured to perform the method according to claim 1.

15. A non-transitory computer-readable storage medium, the storage medium storing a computer program, which, when executed by at least one processor, causes the at least one processor to perform:
    obtaining a molybdenum target image;
    extracting a plurality of candidate regions from the molybdenum target image; and
    marking, in the molybdenum target image, a target region in the plurality of candidate regions by using a neural network model obtained by deep learning training,
    wherein a probability that a lump comprised in the target region is a target lump is greater than a first threshold, a probability that the target lump is a malignant tumor is greater than a second threshold, and the neural network model is used for indicating a mapping relationship between a candidate region and a probability that a lump comprised in the candidate region is the target lump.

16. An image processing apparatus, comprising:
    at least one memory configured to store program code; and
    at least one processor configured to read the program code and operate as instructed by the program code, the program code comprising:
    obtaining code configured to cause at least one of the at least one processor to obtain a molybdenum target image;
    extracting code configured to cause at least one of the at least one processor to extract a plurality of candidate regions from the molybdenum target image; and
    marking code configured to cause at least one of the at least one processor to mark, in the molybdenum target image, a target region in the plurality of candidate regions by using a neural network model obtained by deep learning training,
    wherein a probability that a lump comprised in the target region is a target lump is greater than a first threshold, a probability that the target lump is a malignant tumor is greater than a second threshold, and the neural network model is used for indicating a mapping relationship between a candidate region and a probability that a lump comprised in the candidate region is the target lump.

17. The apparatus according to claim 16, wherein the marking code comprises:

code configured to cause at least one of the at least one processor to obtain, by using the neural network model, a probability that a lump comprised in each candidate region in the plurality of candidate regions is the target lump; and code configured to cause at least one of the at least one processor to determine a candidate region whose probability is greater than the first threshold as the target region, and mark the target region in the molybdenum target image.

18. The apparatus according to claim 16, wherein the program code further comprises:

code configured to cause at least one of the at least one processor to perform deep learning training by using a mapping relationship between a sample lump region and a probability that a lump comprised in the sample lump region is the target lump, to obtain the neural network model, wherein, during the deep learning training, a training input parameter comprises the sample lump region, and a training output parameter comprises the probability that the lump comprised in the sample lump region is the target lump.

19. The apparatus according to claim 18, wherein the sample lump region comprises a first lump region and a second lump region, the first lump region comprises the target lump and the second lump region does not comprise the target lump, and the deep learning training comprises deep learning training by using a mapping relationship between the first lump region and a probability that the lump comprised in the first lump region is the target lump and a mapping relationship between the second lump region and a probability that the lump comprised in the second lump region is the target lump, to obtain the neural network model.

20. The apparatus according to claim 17, wherein, based on a plurality of candidate regions having probabilities of including the target lump that are greater than the first threshold, the marking code further comprises:

code configured to cause at least one of the at least one processor to rank, according to values of the probabilities, the plurality of candidate regions whose probabilities of including the target lump that are greater than the first threshold;

code configured to cause at least one of the at least one processor to calculate an overlapping area between a first candidate region and each second candidate region respectively, the first candidate region being a candidate region having a largest probability of including the target lump among the plurality of candidate regions whose probabilities of including the target lump that are greater than the first threshold, and the second candidate region being a candidate region other than the first candidate region in the plurality of candidate regions whose probabilities of including the target lump that are greater than the first threshold;

code configured to cause at least one of the at least one processor to delete any second candidate region whose overlapping area with the first candidate region is greater than a third threshold from the plurality of candidate regions whose probabilities of including the target lump that are greater than the first threshold, to obtain at least one remaining candidate region; and code configured to cause at least one of the at least one processor to determine the at least one at least one candidate region as the target region.

* * * * *